(12) United States Patent
Dominguez et al.

(10) Patent No.: US 11,071,793 B2
(45) Date of Patent: Jul. 27, 2021

(54) PROBES FOR IMAGING HUNTINGTIN PROTEIN

(71) Applicant: CHDI Foundation, Inc., New York, NY (US)

(72) Inventors: Celia Dominguez, Los Angeles, CA (US); John Wityak, Carlsbad, CA (US); Jonathan Bard, New York, NY (US); Christopher John Brown, Abingdon (GB); Thomas Martin Krülle, Oxford (GB); Daniel Clark-Frew, Wantage (GB); Sarah Hayes, Abingdon (GB)

(73) Assignee: CHDI Foundation, Inc., New York, NY (US)

( * ) Notice: Subject to any disclaimer, the term of this patent is extended or adjusted under 35 U.S.C. 154(b) by 50 days.

(21) Appl. No.: 15/507,214

(22) PCT Filed: Aug. 28, 2015

(86) PCT No.: PCT/US2015/047396
§ 371 (c)(1),
(2) Date: Feb. 27, 2017

(87) PCT Pub. No.: WO2016/033436
PCT Pub. Date: Mar. 3, 2016

(65) Prior Publication Data
US 2017/0281804 A1    Oct. 5, 2017

Related U.S. Application Data

(60) Provisional application No. 62/043,644, filed on Aug. 29, 2014.

(51) Int. Cl.
| | | |
|---|---|---|
| *A61K 51/00* | (2006.01) | |
| *A61M 36/14* | (2006.01) | |
| *A61K 51/04* | (2006.01) | |
| *C07D 401/14* | (2006.01) | |
| *C07D 403/04* | (2006.01) | |
| *C07D 401/04* | (2006.01) | |
| *C07D 487/04* | (2006.01) | |
| *C07D 513/04* | (2006.01) | |
| *C07D 513/14* | (2006.01) | |

(52) U.S. Cl.
CPC ........ *A61K 51/0455* (2013.01); *C07D 401/04* (2013.01); *C07D 401/14* (2013.01); *C07D 403/04* (2013.01); *C07D 487/04* (2013.01); *C07D 513/04* (2013.01); *C07D 513/14* (2013.01); *C07B 2200/05* (2013.01)

(58) Field of Classification Search
CPC .............. A61K 51/0455; C07D 487/04; C07D 513/04; C07D 513/14; C07B 2200/05

USPC ........................................................ 424/1.65
See application file for complete search history.

(56) References Cited

U.S. PATENT DOCUMENTS

| | | | | |
|---|---|---|---|---|
| 5,726,197 | A | * | 3/1998 | Clark ................... C07D 403/04 514/370 |
| 2009/0123416 | A1 | | 5/2009 | Zeldis et al. |
| 2016/0237095 | A1 | * | 8/2016 | Kim ..................... C07D 487/04 |
| 2017/0056535 | A1 | | 3/2017 | Dominguez et al. |
| 2017/0283436 | A1 | | 10/2017 | Dominguez et al. |
| 2017/0283439 | A1 | | 10/2017 | Dominguez et al. |
| 2017/0292150 | A1 | | 10/2017 | Dominguez et al. |
| 2019/0167821 | A1 | | 6/2019 | Dominguez et al. |
| 2020/0102328 | A1 | | 4/2020 | Dominguez et al. |

FOREIGN PATENT DOCUMENTS

| | | | |
|---|---|---|---|
| CN | 101500995 | 8/2009 | |
| EP | 1481679 | 12/2004 | |
| WO | WO 00/76969 | 12/2000 | |
| WO | WO 2009/042907 | 4/2009 | |
| WO | WO-2009072581 A1 * | 6/2009 | ........... C07D 409/10 |
| WO | WO-2010104324 A2 * | 9/2010 | ........... C07D 209/46 |
| WO | WO 2013/161312 | 10/2013 | |

OTHER PUBLICATIONS

Yu et al. Bull Korean Chem Soc 2010, 31, 177-180.*
Suzuki et al. Tetrahedron 2012, 68, 2336-2341.*
Hudson et al. Ann. NY Acad. Sci. 2003, 302-308.*
Bergstrom et al. Eur. J. Clin. Pharmacol. 2003, 59, 357-366. (Year: 2003).*
Extended European Search Report and Opinion dated Mar. 20, 2018 for EP Application No. 15836970.2. 9 pages.
International Search Report & Written Opinion dated Dec. 14, 2015 for PCT/US2015/047396. 9 pages.

(Continued)

*Primary Examiner* — Michael G. Hartley
*Assistant Examiner* — Sean R Donohue
(74) *Attorney, Agent, or Firm* — Sheppard Mullin Richter & Hampton LLP

(57) ABSTRACT

Provided are imaging agents comprising a compound of Formula I, or a pharmaceutically acceptable salt thereof, and methods of their use.

(I)

20 Claims, No Drawings

(56) References Cited

OTHER PUBLICATIONS

Li, et al. In vivo imaging of the metabotropic glutamate receptor 1 (mGluR1) with positron emission tomography: recent advance and perspective. Curr Med Chem. 2014;21(1):113-23.
Tu, et al. Compounds for imaging amyloid-β deposits in an Alzheimer's brain: a patent review. Expert Opin Ther Pat. Apr. 2015;25(4):413-23. doi: 10.1517/13543776.2015.1007953. Epub Mar. 8, 2015.
Guo Zongru. Effect of changes in groups on activity, Medicinal Chemistry (2nd edition), pp. 128-130, China Medical Science Press, published on Aug. 31, 2003.

* cited by examiner

PROBES FOR IMAGING HUNTINGTIN PROTEIN

CROSS REFERENCE TO RELATED APPLICATIONS

This application is a U.S. National Stage Application under 35 U.S.C. § 371 of PCT Application No. PCT/US2015/047396, filed Aug. 28, 2015, which claims priority to U.S. Provisional Application No. 62/043,644, filed Aug. 29, 2014, which is incorporated herein by reference for all purposes.

The advent of molecular imaging approaches such as positron emission tomography (PET) and single photon emission computed tomography (SPECT) has enabled measurements of molecular and cellular mechanisms throughout the body in preclinical and clinical settings. Such measurements have widespread diagnostic utility and their use for evaluation of treatment responses and to assist drug development is expanding rapidly. The recent introduction of high-resolution molecular imaging technology is considered by many experts as a major breakthrough that will potentially lead to a revolutionary paradigm shift in health care and revolutionize clinical practice.

PET involves the administration to a subject of a positron-emitting radionuclide tracer followed by detection of the positron emission (annihilation) events in the body. The radionuclide tracer is typically composed of a targeting molecule having incorporated therein one or more types of positron-emitting radionuclides.

Many new molecular probes labeled with positron-emitting radionuclides and associated PET imaging assays are under development to target, detect, visualize, and quantify various extracellular and intracellular molecules and processes associated with diseases such as cancer, heart disease, and neurological disorders. For instance, several types of agents have been synthesized and evaluated for imaging amyloid β (Aβ) plaques in patients with Alzheimer's disease (AD) including, arylbenzothiazoles, stilbenes, imidazopyridines, pyridylbenzothiazoles, pyridylbenzoxazoles and pyridylbenzofurans (Swahn et al., *Bioorganic & Medicinal Chemistry Letters*, 20 (2010) 1976-1980). Furthermore, styrylbenzimidazole (SBIM) derivatives have been developed as agents for imaging neurofibrillary tangles (NFT), composed of hyperphosphorylated tau protein, in patients with AD. In binding experiments using recombinant tau and amyloid $β_{1-42}$ ($Aβ_{1-42}$) aggregates, 4-[(E)-2-(6-iodo-1H-benzimidazol-2-yl)ethenyl]-N,N-dimethylaniline (SBIM-3) showed higher affinity for the tau aggregates than $Aβ_{1-42}$ aggregates (ratio of $K_d$ values was 2.73). In in vitro autoradiography and fluorescent staining, [$^{125}$I]SBIM-3 (or SBIM-3) bound NFT in sections of AD brain tissue. In biodistribution experiments using normal mice, all [$^{125}$I]SBIM derivatives showed high initial uptake into (3.20-4.11% ID/g at 2 min after the injection) and rapid clearance from (0.12-0.33% ID/g at 60 min after the injection) the brain (Matsumura et al., *Bioorganic & Medicinal Chemistry*, 21 (2013) 3356-3362).

Huntington's disease (HD) is an inherited progressive neurodegenerative disorder, characterized by motor, cognitive, and psychiatric deficits as well as neurodegeneration and brain atrophy beginning in the striatum and the cortex and extending to other subcortical brain regions. It belongs to a family of neurodegenerative diseases caused by mutations in which an expanded CAG repeat tract results in long stretches of polyglutamine (polyQ) in the encoded protein. This family also includes dentatorubral-pallidoluysian atrophy (DRPLA), spinal and bulbar muscular atrophy (SBMA) and the spinocerebellar ataxias (SCAs). Apart from their polyQ repeats, the proteins involved are unrelated, and although they are all widely expressed in the central nervous system and peripheral tissues, they lead to characteristic patterns of neurodegeneration. In HD, the selective neurodegeneration of the γ-aminobutyric acid-releasing spiny-projection neurons of the striatum is predominant, although loss of neurons in many other brain regions has also been reported. In the unaffected population, the number of CAG repeats in the 11'15 gene that encodes the HD protein huntingtin (HTT protein) varies from 6 to 35; repeats of 36 or more define an HD allele. The length of the CAG expansion is inversely correlated with age of disease onset, with cases of juvenile onset characterized by expansions of more than 60 repeats. HD has a prevalence of 5-10 cases per 100,000 worldwide, which makes it the most common inherited neurodegenerative disorder. HTT protein is a 348-kDa multidomain protein that contains a polymorphic glutamine/proline-rich domain at its amino-terminus. The longer polyQ domain seems to induce conformational changes in the protein, which causes it to form intracellular aggregates that, in most cases, manifest as nuclear inclusions. However, aggregates can also form outside the nucleus. HTT protein is present in the nucleus, cell body, dendrites and nerve terminals of neurons, and is also associated with a number of organelles including the Golgi apparatus, endoplasmic reticulum and mitochondria.

Several clinical trials are investigating means to alleviate or reduce symptoms and slow progression in clinically diagnosed HD. Consistent with other medical conditions, treatments might be ideally initiated at or before the earliest signs of disease. There are at least two primary challenges to the design of clinical trials for pre-HD: selection of participants who are most likely to show measurable change over the course of a clinical trial, and development of outcome measures that are sensitive to interventions and can demonstrate variation over the natural history of pre-HD. In order to meet these and other challenges to preventive clinical trials, indicators of very early disease are required.

In view of the central role of the accumulation of aggregated forms of HTT protein in the pathogenesis of HD, there is a need for molecular probes that bind to such abnormalities with high sensitivity and specificity, for molecular imaging in the living subject using PET. The compounds described herein meet this and other needs.

Provided is an imaging agent comprising a compound of Formula I, or a pharmaceutically acceptable salt thereof,

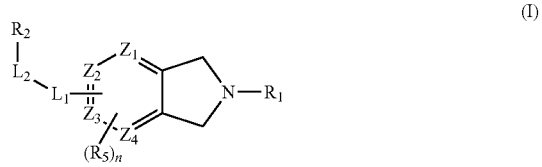

wherein
$Z_1$, $Z_2$, $Z_3$, and $Z_4$ are independently chosen from CH and N, provided that at least two of $Z_1$, $Z_2$, $Z_3$, and $Z_4$ are CH;
$R_1$ is chosen from aryl, heteroaryl, and heterocycloalkenyl, each of which is optionally substituted with one or two groups independently chosen from alkynyl, heteroaryl, cyano, optionally substituted amino, halo, lower alkyl, and lower alkyl substituted with optionally substituted amino;

$L_1$ is chosen from 0 and $NR_4$;

$R_4$ is chosen from hydrogen and lower alkyl;

$L_2$ is $(CH_2)_m$ where m is 0, 1, or 2; and $R_2$ is chosen from hydrogen, aryl, aryl substituted with hydroxyl or lower alkoxy, heteroaryl, and heteroaryl substituted with hydroxyl or lower alkoxy, $R_5$ is chosen from lower alkyl, lower alkoxy, halo, and oxo (as a substituent on the heterocycloalkyl ring); and n is 0 or 1;

wherein the compound of Formula I, or a pharmaceutically acceptable salt there of, is labeled with one or more positron-emitting radionuclides.

Also provided is a method of generating diagnostic images in an individual comprising administering an effective amount of an imaging agent described herein to an individual, and generating an image of at least a part of said individual.

As used in the present specification, the following words, phrases and symbols are generally intended to have the meanings as set forth below, except to the extent that the context in which they are used indicates otherwise. The following abbreviations and terms have the indicated meanings throughout:

A dash ("—") that is not between two letters or symbols is used to indicate a point of attachment for a substituent. For example, —$CONH_2$ is attached through the carbon atom.

As used herein the terms "group", "radical" or "fragment" refer to a functional group or fragment of a molecule attachable to a bond or other fragments of molecules.

When a range of values is given (e.g., $C_{1-6}$ alkyl), each value within the range as well as all intervening ranges are included. For example, "$C_{1-6}$ alkyl" includes $C_1$, $C_2$, $C_3$, $C_4$, $C_5$, $C_6$, $C_{1-6}$, $C_{2-6}$, $C_{3-6}$, $C_{4-6}$, $C_{5-6}$, $C_{1-5}$, $C_{2-5}$, $C_{3-5}$, $C_{4-5}$, $C_{1-4}$, $C_{2-4}$, $C_{3-4}$, $C_{1-3}$, $C_{2-3}$, and $C_{1-2}$ alkyl.

When a moiety is defined as being optionally substituted, it may be substituted as itself or as part of another moiety. For example, if Rx is defined as "$C_{1-6}$ alkyl or $OC_{1-6}$ alkyl, wherein $C_{1-6}$ alkyl is optionally substituted with halogen", then both the $C_{1-6}$ alkyl group alone and the $C_{1-6}$ alkyl that makes up part of the $OC_{1-6}$ alkyl group may be substituted with halogen.

The term "alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl residue having a specific number of carbons is named, all geometric isomers having that number of carbons are intended to be encompassed; thus, for example, "butyl" is meant to include n-butyl, sec-butyl, isobutyl and tert-butyl; "propyl" includes n-propyl and isopropyl. "Lower alkyl" refers to alkyl groups having 1 to 6 carbons.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentyloxy, and the like. Alkoxy groups will usually have from 1 to 6 carbon atoms attached through the oxygen bridge. "Lower alkoxy" refers to alkoxy groups having 1 to 6 carbons. By "cycloalkoxy" is meant a cycloalkyl group that is likewise attached through an oxygen bridge.

"Alkynyl" refers to an unsaturated branched or straight-chain alkyl group having the indicated number of carbon atoms (e.g., 2 to 8 or 2 to 6 carbon atoms) and at least one carbon-carbon triple bond derived by the removal of two molecules of hydrogen from adjacent carbon atoms of the corresponding alkyl. Alkynyl groups include, but are not limited to, ethynyl, propynyl (e.g., prop-1-yn-1-yl, prop-2-yn-1-yl) and butynyl (e.g., but-1-yn-1-yl, but-1-yn-3-yl, but-3-yn-1-yl). "Lower alkynyl" refers to alkynyl groups having 2 to 6 carbons.

"Aryl" indicates an aromatic carbon ring having the indicated number of carbon atoms, for example, 6 to 12 or 6 to 10 carbon atoms. Aryl groups may be monocyclic or polycyclic (e.g., bicyclic, tricyclic). In some instances, both rings of a polycyclic aryl group are aromatic (e.g., naphthyl). In other instances, polycyclic aryl groups may include a non-aromatic ring (e.g., cycloalkyl, cycloalkenyl, heterocycloalkyl, heterocycloalkenyl) fused to an aromatic ring, provided the polycyclic aryl group is bound to the parent structure via an atom in the aromatic ring. Thus, a 1,2,3,4-tetrahydronaphthalen-5-yl group (wherein the moiety is bound to the parent structure via an aromatic carbon atom) is considered an aryl group, while 1,2,3,4-tetrahydronaphthalen-1-yl (wherein the moiety is bound to the parent structure via a non-aromatic carbon atom) is not considered an aryl group. Similarly, a 1,2,3,4-tetrahydroquinolin-8-yl group (wherein the moiety is bound to the parent structure via an aromatic carbon atom) is considered an aryl group, while 1,2,3,4-tetrahydroquinolin-1-yl group (wherein the moiety is bound to the parent structure via a non-aromatic nitrogen atom) is not considered an aryl group. However, the term "aryl" does not encompass or overlap with "heteroaryl" regardless of the point of attachment (e.g., both quinolin-5-yl and quinolin-2-yl are heteroaryl groups). In some instances, aryl is phenyl or naphthyl. In certain instances, aryl is phenyl.

Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

"Cycloalkyl" indicates a non-aromatic, fully saturated carbocyclic ring having the indicated number of carbon atoms, for example, 3 to 10, or 3 to 8, or 3 to 6 ring carbon atoms. Cycloalkyl groups may be monocyclic or polycyclic (e.g., bicyclic, tricyclic). Examples of cycloalkyl groups include cyclopropyl, cyclobutyl, cyclopentyl, and cyclohexyl, as well as bridged and caged ring groups (e.g., norbornane, bicyclo[2.2.2]octane). In addition, one ring of a polycyclic cycloalkyl group may be aromatic, provided the polycyclic cycloalkyl group is bound to the parent structure via a non-aromatic carbon. For example, a 1,2,3,4-tetrahydronaphthalen-1-yl group (wherein the moiety is bound to the parent structure via a non-aromatic carbon atom) is a cycloalkyl group, while 1,2,3,4-tetrahydronaphthalen-5-yl (wherein the moiety is bound to the parent structure via an aromatic carbon atom) is not considered a cycloalkyl group.

"Cycloalkenyl" indicates a non-aromatic carbocyclic ring, containing the indicated number of carbon atoms (e.g., 3 to 10, or 3 to 8, or 3 to 6 ring carbon atoms) and at least one carbon-carbon double bond derived by the removal of one molecule of hydrogen from adjacent carbon atoms of the corresponding cycloalkyl. Cycloalkenyl groups may be monocyclic or polycyclic (e.g., bicyclic, tricyclic). Examples of cycloalkenyl groups include cyclopropenyl, cyclobutenyl, cyclopentenyl, cyclopentadienyl, and cyclohexenyl, as well as bridged and caged ring groups (e.g., bicyclo[2.2.2]octene). In addition, one ring of a polycyclic cycloalkenyl group may be aromatic, provided the polycyclic alkenyl group is bound to the parent structure via a non-aromatic carbon atom. For example, inden-1-yl (wherein the moiety is bound to the parent structure via a non-aromatic carbon atom) is considered a cycloalkenyl group, while inden-4-yl (wherein the moiety is bound to the parent structure via an aromatic carbon atom) is not considered a cycloalkenyl group.

The term "halo" includes fluoro, chloro, bromo, and iodo, and the term "halogen" includes fluorine, chlorine, bromine, and iodine.

"Haloalkyl" includes straight and branched carbon chains having the indicated number of carbon atoms (e.g., 1 to 6 carbon atoms) substituted with at least one halogen atom. In instances wherein the haloalkyl group contains more than one halogen atom, the halogens may be the same (e.g., dichloromethyl) or different (e.g., chlorofluoromethyl). Examples of haloalkyl groups include, but are not limited to, chloromethyl, dichloromethyl, trichloromethyl, fluoromethyl, difluoromethyl, trifluoromethyl, chlorofluoromethyl, 2-fluoroethyl, 2,2-difluoroethyl, 2,2,2-trifluoroethyl, 1,2-difluoroethyl, 2-chloroethyl, 2,2-dichloroethyl, 2,2,2-trichloroethyl, 1,2-dichloroethyl, pentachloroethyl, and pentafluoroethyl.

"Heteroaryl" indicates an aromatic ring containing the indicated number of atoms (e.g., 5 to 12, or 5 to 10 membered heteroaryl) made up of one or more heteroatoms (e.g., 1, 2, 3 or 4 heteroatoms) selected from N, O and S and with the remaining ring atoms being carbon. Heteroaryl groups do not contain adjacent S and O atoms. In some embodiments, the total number of S and O atoms in the heteroaryl group is not more than 2. In some embodiments, the total number of S and O atoms in the heteroaryl group is not more than 1. Unless otherwise indicated, heteroaryl groups may be bound to the parent structure by a carbon or nitrogen atom, as valency permits. For example, "pyridyl" includes 2-pyridyl, 3-pyridyl and 4-pyridyl groups, and "pyrrolyl" includes 1-pyrrolyl, 2-pyrrolyl and 3-pyrrolyl groups. When nitrogen is present in a heteroaryl ring, it may, where the nature of the adjacent atoms and groups permits, exist in an oxidized state (i.e., $N^+$—$O^-$). Additionally, when sulfur is present in a heteroaryl ring, it may, where the nature of the adjacent atoms and groups permits, exist in an oxidized state (i.e., $S^+$—$O^-$ or $SO_2$). Heteroaryl groups may be monocyclic or polycyclic (e.g., bicyclic, tricyclic).

In some instances, a heteroaryl group is monocyclic. Examples include pyrrole, pyrazole, imidazole, triazole (e.g., 1,2,3-triazole, 1,2,4-triazole, 1,3,4-triazole), tetrazole, furan, isoxazole, oxazole, oxadiazole (e.g., 1,2,3-oxadiazole, 1,2,4-oxadiazole, 1,3,4-oxadiazole), thiophene, isothiazole, thiazole, thiadiazole (e.g., 1,2,3-thiadiazole, 1,2,4-thiadiazole, 1,3,4-thiadiazole), pyridine, pyridazine, pyrimidine, pyrazine, triazine (e.g., 1,2,4-triazine, 1,3,5-triazine) and tetrazine.

In some instances, both rings of a polycyclic heteroaryl group are aromatic. Examples include indole, isoindole, indazole, benzoimidazole, benzotriazole, benzofuran, benzoxazole, benzoisoxazole, benzoxadiazole, benzothiophene, benzothiazole, benzoisothiazole, benzothiadiazole, 1H-pyrrolo[2,3-b]pyridine, 1H-pyrazolo[3,4-b]pyridine, 3H-imidazo[4,5-b]pyridine, 3H-[1,2,3]triazolo[4,5-b]pyridine, 1H-pyrrolo[3,2-b]pyridine, 1H-pyrazolo[4,3-b]pyridine, 1H-imidazo[4,5-b]pyridine, 1H[1,2,3]triazolo[4,5-b]pyridine, 1H-pyrrolo[2,3-c]pyridine, 1H-pyrazolo[3,4-c]pyridine, 3H-imidazo[4,5-c]pyridine, 3H-[1,2,3]triazolo[4,5-c]pyridine, 1H-pyrrolo[3,2-c]pyridine, 1H-pyrazolo[4,3-c]pyridine, 1H-imidazo[4,5-c]pyridine, 1H-[1,2,3]triazolo[4,5-c]pyridine, furo[2,3-b]pyridine, oxazolo[5,4-b]pyridine, isoxazolo[5,4-b]pyridine, [1,2,3]oxadiazolo[5,4-b]pyridine, furo[3,2-b]pyridine, oxazolo[4,5-b]pyridine, isoxazolo[4,5-b]pyridine, [1,2,3]oxadiazolo[4,5-b]pyridine, furo[2,3-c]pyridine, oxazolo[5,4-c]pyridine, isoxazolo[5,4-c]pyridine, [1,2,3]oxadiazolo[5,4-c]pyridine, furo[3,2-c]pyridine, oxazolo[4,5-c]pyridine, isoxazolo[4,5-c]pyridine, [1,2,3]oxadiazolo[4,5-c]pyridine, thieno[2,3-b]pyridine, thiazolo[5,4-b]pyridine, isothiazolo[5,4-b]pyridine, [1,2,3]thiadiazolo[5,4-b]pyridine, thieno[3,2-b]pyridine, thiazolo[4,5-b]pyridine, isothiazolo[4,5-b]pyridine, [1,2,3]thiadiazolo[4,5-b]pyridine, thieno[2,3-c]pyridine, thiazolo[5,4-c]pyridine, isothiazolo[5,4-c]pyridine, [1,2,3]thiadiazolo[5,4-c]pyridine, thieno[3,2-c]pyridine, thiazolo[4,5-c]pyridine, isothiazolo[4,5-c]pyridine, [1,2,3]thiadiazolo[4,5-c]pyridine, quinoline, isoquinoline, cinnoline, quinazoline, quinoxaline, phthalazine, naphthyridine (e.g., 1,8-naphthyridine, 1,7-naphthyridine, 1,6-naphthyridine, 1,5-naphthyridine, 2,7-naphthyridine, 2,6-naphthyridine), imidazo[1,2-a]pyridine, 1H-pyrazolo[3,4-d]thiazole, 1H-pyrazolo[4,3-d]thiazole and imidazo[2,1-b]thiazole.

In other instances, polycyclic heteroaryl groups may include a non-aromatic ring (e.g., cycloalkyl, cycloalkenyl, heterocycloalkyl, heterocycloalkenyl) fused to a heteroaryl ring, provided the polycyclic heteroaryl group is bound to the parent structure via an atom in the aromatic ring. For example, a 4,5,6,7-tetrahydrobenzo[d]thiazol-2-yl group (wherein the moiety is bound to the parent structure via an aromatic carbon atom) is considered a heteroaryl group, while 4,5,6,7-tetrahydrobenzo[d]thiazol-5-yl (wherein the moiety is bound to the parent structure via a non-aromatic carbon atom) is not considered a heteroaryl group.

"Heterocycloalkyl" indicates a non-aromatic, fully saturated ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon. Heterocycloalkyl groups may be monocyclic or polycyclic (e.g., bicyclic, tricyclic).

Examples of monocyclic heterocycloalkyl groups include oxiranyl, aziridinyl, azetidinyl, pyrrolidinyl, imidazolidinyl, pyrazolidinyl, piperidinyl, piperazinyl, morpholinyl and thiomorpholinyl.

When nitrogen is present in a heterocycloalkyl ring, it may, where the nature of the adjacent atoms and groups permits, exist in an oxidized state (i.e., $N^+$—$O^-$). Examples include piperidinyl N-oxide and morpholinyl-N-oxide. Additionally, when sulfur is present in a heterocycloalkyl ring, it may, where the nature of the adjacent atoms and groups permits, exist in an oxidized state (i.e., $S^+$—$O^-$ or —$SO_2$—). Examples include thiomorpholine S-oxide and thiomorpholine S,S-dioxide.

In addition, one ring of a polycyclic heterocycloalkyl group may be aromatic (e.g., aryl or heteroaryl), provided the polycyclic heterocycloalkyl group is bound to the parent structure via a non-aromatic carbon or nitrogen atom. For example, a 1,2,3,4-tetrahydroquinolin-1-yl group (wherein the moiety is bound to the parent structure via a non-aromatic nitrogen atom) is considered a heterocycloalkyl group, while 1,2,3,4-tetrahydroquinolin-8-yl group (wherein the moiety is bound to the parent structure via an aromatic carbon atom) is not considered a heterocycloalkyl group.

"Heterocycloalkenyl" indicates a non-aromatic ring having the indicated number of atoms (e.g., 3 to 10, or 3 to 7, membered heterocycloalkyl) made up of one or more heteroatoms (e.g., 1, 2, 3 or 4 heteroatoms) selected from N, O and S and with the remaining ring atoms being carbon, and at least one double bond derived by the removal of one molecule of hydrogen from adjacent carbon atoms, adjacent nitrogen atoms, or adjacent carbon and nitrogen atoms of the corresponding heterocycloalkyl. Heterocycloalkenyl groups may be monocyclic or polycyclic (e.g., bicyclic, tricyclic). When nitrogen is present in a heterocycloalkenyl ring, it may, where the nature of the adjacent atoms and groups permits, exist in an oxidized state (i.e., $N^+$—$O^-$). Additionally, when sulfur is present in a heterocycloalkenyl ring, it may, where the nature of the adjacent atoms and groups permits, exist in an oxidized state (i.e., $S^+$—$O^-$ or —$SO_2$—). Examples of heterocycloalkenyl groups include dihydrofuranyl (e.g., 2,3-dihydrofuranyl, 2,5-dihydrofuranyl), dihydrothiophenyl (e.g., 2,3-dihydrothiophenyl, 2,5-dihydrothiophenyl), dihydropyrrolyl (e.g., 2,3-dihydro-1H-pyrrolyl, 2,5-dihydro-1H-pyrrolyl), dihydroimidazolyl (e.g., 2,3-dihydro-1H-imidazolyl, 4,5-dihydro-1H-imidazolyl), pyranyl, dihydropyranyl (e.g., 3,4-dihydro-2H-pyranyl, 3,6-dihydro-2H-pyranyl), tetrahydropyridinyl (e.g., 1,2,3,4-tetrahydropyridinyl, 1,2,3,6-tetrahydropyridinyl) and dihydropyridine (e.g., 1,2-dihydropyridine, 1,4-dihydropyridine). In addition, one ring of a polycyclic heterocycloalkenyl group may be aromatic (e.g., aryl or heteroaryl), provided the polycyclic heterocycloalkenyl group is bound to the parent structure via a non-aromatic carbon or nitrogen atom. For example, a 1,2-dihydroquinolin-1-yl group (wherein the moiety is bound to the parent structure via a non-aromatic nitrogen atom) is considered a heterocycloalkenyl group, while 1,2-dihydroquinolin-8-yl group (wherein the moiety is bound to the parent structure via an aromatic carbon atom) is not considered a heterocycloalkenyl group.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined herein. It will be understood by those skilled in the art, with respect to any group containing one or more substituents, that such groups are not intended to introduce any substitution or substitution patterns that are sterically impractical, synthetically non-feasible, and/or inherently unstable.

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl (including without limitation $C_1$-$C_4$ alkyl), cycloalkyl, cycloalkenyl, aryl, heterocycloalkyl, heterocycloalkenyl, and heteroaryl, unless otherwise expressly defined, refer respectively to alkyl, cycloalkyl, cycloalkenyl, aryl, heterocycloalkyl, heterocycloalkenyl, and heteroaryl, herein one or more (such as up to 5, for example, up to 3) hydrogen atoms are replaced by a substituent independently chosen from:

—$R^a$, —$OR^b$, —$O(C_1$-$C_2$ alkyl)O— (e.g., methylenedioxy-), —$SR^b$, guanidine (—NHC(=NH)NH$_2$), guanidine wherein one or more of the guanidine hydrogens are replaced with a $C_1$-$C_4$alkyl group, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^c$ $CONR^bR^c$, —$SOR^a$, —$SO_2R^a$, —$SO_2NR^bR^c$, and —$NR^cSO_2R^a$, where $R^a$ is chosen from $C_1$-$C_6$ alkyl, cycloalkyl, aryl, heterocycloalkyl, and heteroaryl;

$R^b$ is chosen from H, $C_1$-$C_6$ alkyl, aryl, and heteroaryl; and $R^c$ is chosen from hydrogen and $C_1$-$C_4$alkyl; or $R^b$ and $R^c$, and the nitrogen to which they are attached, form a heterocycloalkyl group; and where each $C_1$-$C_6$ alkyl, cycloalkyl, aryl, heterocycloalkyl, and heteroaryl is optionally substituted with one or more, such as one, two, or three, substituents independently selected from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), N($C_1$-$C_4$ alkyl)($C_1$-$C_4$ alkylheteroaryl), —NH($C_1$-$C_4$ alkylphenyl), cyano, nitro, oxo (as a substituent for heteroaryl), —$CO_2H$, —$C(O)OC_1$-$C_4$alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O) (phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$ ($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$ ($C_1$-$C_4$ haloalkyl).

The term "substituted amino" refers to the group —$NHR^d$ or —$NR^dR^d$ where each $R^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —$O(C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, $OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^e$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), N($C_1$-$C_4$ alkyl)($C_1$-$C_4$ alkylheteroaryl), —NH($C_1$-$C_4$ alkylphenyl), cyano, nitro, oxo (as a substitutent for heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" also refers to the group —NR$^e$R$^f$ wherein R$^e$ and R$^f$, together with the nitrogen to which they are bound, form an optionally substituted 5- to 7-membered nitrogen-containing, non-aromatic, heterocycle which optionally contains 1 or 2 additional heteroatoms chosen from nitrogen, oxygen, and sulfur.

"Aminocarbonyl" encompasses a group of the formula —(C═O)(optionally substituted amino) wherein substituted amino is as described herein.

Compounds described herein include, but are not limited to, their optical isomers, racemates, and other mixtures thereof. In those situations, the single enantiomers or diastereoisomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. The term "isomers" refers to different compounds that have the same molecular formula. The term "stereoisomers" refers to isomers that differ only in the way the atoms are arranged in space. The term "enantiomers" refers to stereoisomers that are non-superimposable mirror images of each other. A 1:1 mixture of a pair of enantiomers is a "racemic" mixture. The symbol "(±)" may be used to designate a racemic mixture where appropriate. The term "diastereoisomers" refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line.

Where compounds described herein exist in various tautomeric forms, the term "compound" includes all tautomeric forms of the compound. Such compounds also include crystal forms including polymorphs and clathrates. Similarly, the term "salt" includes all tautomeric forms and crystal forms of the compound. The term "tautomers" refers to structurally distinct isomers that interconvert by tautomerization. Tautomerization is a form of isomerization and includes prototropic or proton-shift tautomerization, which is considered a subset of acid-base chemistry. Prototropic tautomerization or proton-shift tautomerization involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Pharmaceutically acceptable forms of the compounds recited herein include pharmaceutically acceptable salts, and mixtures thereof. In some embodiments, the compounds described herein are in the form of pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, haloalkanoate such as trifluoroacetate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

The term "administering", as used herein in conjunction with a diagnostic agent, such as, for example, a positron-emitter labeled compound described herein, means administering directly into or onto a target tissue or to administer the diagnostic agent systemically to a patient whereby the diagnostic agent is used to image the tissue or a pathology associated with the tissue to which it is targeted. "Administering" a composition may be accomplished by injection, infusion, or by either method in combination with other known techniques.

The term "Curie" (Ci) is a unit of measurement of radioactivity. One Ci refers to that amount of any radioactive material that will decay at a rate of $3.7 \times 10^{10}$ disintegrations per second. The term "milliCurie" (mCi) refers to $10^{-3}$ Curie. It is understood that the International System (SI) unit of radioactivity, the Becquerel, is equal to one disintegration/second. Thus one Becquerel=$2.7 \times 10^{-11}$ Curie.

The term "diagnostic imaging", as used herein, refers to the use of electromagnetic radiation to produce images of internal structures of the human or animal body for the purpose of diagnosis.

The term "effective amount" of a compound, as used herein, is a predetermined amount calculated to achieve a desired effect such as an amount sufficient to enable the acquisition of a desired image of the target organ of an individual. In some instances the target organ is the brain.

The term "huntingtin protein" or "HTT protein", as used herein, refers to the protein encoded by the human huntingtin gene (HTT gene) located on the short (p) arm of chromosome 4 at position 16.3. More precisely, the $IT_{15}$ gene coding for the HTT protein is located from base pair 3,076,407 to base pair 3,245,686 on chromosome 4.

The term "HTT protein aggregate", as used herein refers to an insoluble fibrous amyloid comprising mis-folded HTT protein molecules.

The term "β-amyloid aggregate", as used herein refers to an insoluble fibrous amyloid comprising mis-folded β-amyloid protein molecules.

The term "imaging agent", as used herein, refers to a compound as described herein labeled with one or more positron-emitting isotopes or radionuclides. A positron-emitter labeled compound need only be enriched with a detectable isotope to a degree that permits detection with a technique suitable for the particular application.

The term "pathologic process", as used herein, refers to an altered endogenous biological process that may be associated with the aberrant production and/or functioning of proteins, peptides, RNA and other substances associated with such biological process.

The term "PET imaging", as used herein, refers to the use of a positron-emitter labeled compound to produce images of internal structures of the human or animal body.

The term "pharmaceutical composition" refers to a composition comprising at least one imaging agent described herein, whereby the composition is amenable to investigation for a specified, efficacious outcome in a mammal (for example, without limitation, a human). Those of ordinary skill in the art will understand and appreciate the techniques appropriate for determining whether a composition has a desired efficacious outcome based upon the needs of the artisan.

The term "positron-emitting radionuclide", as used herein, refers to a radioactive isotope that exhibits particular type of radioactive decay referred to as $13_+$ decay, in which a proton inside a radionuclide nucleus is converted into a neutron while releasing a positron and an electron neutrino ($v_e$). Some examples of positron-emitting radionuclides include $^{15}O$, $^{13}N$, $^{11}C$, $^{18}F$, $^{76}Br$, and $^{124}I$. These radionuclides have half-lives of about 2, 10, 20, 110 minutes, 16 hours, and 4.2 days respectively.

The term "tomography", as used herein, refers to a process of imaging by sections. The images may be looked at individually, as a series of two-dimensional slices or together, as a computer-generated three-dimensional representation.

Provided is an imaging agent comprising a compound of Formula I, or a pharmaceutically acceptable salt thereof, (I)

wherein
$Z_1$, $Z_2$, $Z_3$, and $Z_4$ are independently chosen from CH and N, provided that at least two of $Z_1$, $Z_2$, $Z_3$, and $Z_4$ are CH;
$R_1$ is chosen from aryl, heteroaryl, and heterocycloalkenyl, each of which is optionally substituted with one or two groups independently chosen from alkynyl, heteroaryl, cyano, optionally substituted amino, halo, lower alkyl, and lower alkyl substituted with optionally substituted amino;
$L_1$ is chosen from O and $NR_4$;
$R_4$ is chosen from hydrogen and lower alkyl;
$L_2$ is $(CH_2)_m$ where m is 0, 1, or 2; and
$R_2$ is chosen from hydrogen, aryl, aryl substituted with hydroxyl or lower alkoxy, heteroaryl, and heteroaryl substituted with hydroxyl or lower alkoxy,
$R_5$ is chosen from lower alkyl, lower alkoxy, halo, and oxo (as a substituent on the heterocycloalkyl ring); and
n is 0 or 1;
wherein the compound of Formula I, or a pharmaceutically acceptable salt there of, is labeled with one or more positron-emitting radionuclides Also provided is an imaging agent comprising a compound of Formula I, or a pharmaceutically acceptable salt thereof, (I)

wherein
$Z_1$, $Z_2$, $Z_3$, and $Z_4$ are independently chosen from CH and N, provided that at least two of $Z_1$, $Z_2$, $Z_3$, and $Z_4$ are CH;
$R_1$ is chosen from aryl and heteroaryl, each of which is optionally substituted with one or two groups independently chosen from alkynyl, cyano, optionally substituted amino, halo, lower alkyl, and lower alkyl substituted with optionally substituted amino;
$L_1$ is chosen from O and $NR_4$;
$R_4$ is chosen from hydrogen and lower alkyl;
$L_2$ is $(CH_2)_m$ where m is 0, 1, or 2; and
$R_2$ is chosen from hydrogen, heteroaryl, and heteroaryl substituted with hydroxyl or lower alkoxy,
$R_5$ is chosen from lower alkyl, lower alkoxy, and halo; and
n is 0 or 1;
wherein the compound of Formula I, or a pharmaceutically acceptable salt there of, is labeled with one or more positron-emitting radionuclides.

In some embodiments, $R_1$ is phenyl optionally substituted with one or two groups independently chosen from cyano, optionally substituted amino, halo, lower alkyl, and lower alkyl substituted with optionally substituted amino.

In some embodiments, $R_1$ is phenyl optionally substituted with one or two groups independently chosen from cyano, methyl, and methyl substituted with amino, (alkyl)amino or (dialkyl)amino.

In some embodiments, $R_1$ is 2-cyanophenyl.

In some embodiments, $R_1$ is heteroaryl optionally substituted with one or two groups independently chosen from alkynyl, cyano, optionally substituted amino, halo, lower alkyl, and lower alkyl substituted with optionally substituted amino.

In some embodiments, $R_1$ is chosen from pyridine-4-yl, pyridine-2-yl, pyridine-3-yl, pyrimidine-4-yl, 1,2-dihydropyridin-2-one-3-yl, 1H-indazole-4-yl, and 1H-indazole-7-yl, each of which is optionally substituted with one or two groups independently chosen from alkynyl, cyano, optionally substituted amino, halo, lower alkyl, and lower alkyl substituted with optionally substituted amino.

In some embodiments, $R_1$ is chosen from pyridine-4-yl, pyridine-2-yl, pyridine-3-yl, and pyrimidine-4-yl, each of which is optionally substituted with one or two groups independently chosen from alkynyl, cyano, optionally substituted amino, halo, lower alkyl, and lower alkyl substituted with optionally substituted amino.

In some embodiments, $R_1$ is chosen from 5-cyano-pyrimidine-4-yl, pyridine-4-yl, 5-bromo-1,2-dihydropyridin-2-one-3-yl, 3-acetamido-pyridine-4-yl, 2-acetamido-pyridine-6-yl, 3-cyano-pyridine-4-yl, 3-cyano-pyridine-6-yl, 3-bromo-pyridine-4-yl, 3-bromo-pyridine-2-yl, 3-cyano-pyridine-2-yl, 3-fluoro-pyridine-4-yl, 2-cyano-pyridine-4-yl, 4-cyano-pyridine-3-yl, and 3-ethynyl-pyridine-4-yl.

In some embodiments, $R_1$ is pyridine-4-yl or 3-cyano-pyridine-4-yl.

In some embodiments, $R_1$ is heterocycloalkenyl optionally substituted with lower alkyl.

In some embodiments, $R_1$ is 2,3-dihydropyridazine-6-yl optionally substituted with lower alkyl.

In some embodiments, $L_1$ is O.

In some embodiments, m is 1.

In some embodiments, $R_2$ is chosen from hydrogen, aryl, aryl substituted with hydroxyl or lower alkoxy, heteroaryl, and heteroaryl substituted with hydroxyl or lower alkoxy.

In some embodiments, $R_2$ is chosen from hydrogen, heteroaryl, and heteroaryl substituted with hydroxyl or lower alkoxy.

In some embodiments, $R_2$ is chosen from hydrogen, phenyl, pyridine-2-yl, pyrimidine-5-yl, pyrazin-2-yl, and pyrimidin-5-yl, each of which, other than hydrogen, is optionally substituted with hydroxyl or lower alkoxy.

In some embodiments, $R_2$ is chosen from hydrogen, pyridine-2-yl, pyrimidine-5-yl, pyrazin-2-yl, and pyrimidin-5-yl, each of which, other than hydrogen, is optionally substituted with hydroxyl or lower alkoxy.

In some embodiments, $Z_1$, $Z_2$, $Z_3$, and $Z_4$ are CH.

In some embodiments, $Z_1$ is N and $Z_2$, $Z_3$, and $Z_4$ are CH.

In some embodiments, $Z_2$ is N and $Z_1$, $Z_3$, and $Z_4$ are CH.

In some embodiments, $Z_2$ and $Z_4$ are N and $Z_1$ and $Z_3$ are CH.

Also provided is an imaging agent comprising a compound of Formula I is chosen from 2-(5-methoxy-2,3-dihydro-1H-isoindol-2-yl)pyridine-3-carbonitrile;
2-{5-[(5-methoxypyridin-2-yl)methoxy]-2,3-dihydro-1H-isoindol-2-yl}pyridine-3-carbonitrile;
2-[5-(pyrimidin-5-ylmethoxy)-2,3-dihydro-1H-isoindol-2-yl]pyridine-3-carbonitrile;
4-{5-[(5-methoxypyridin-2-yl)methoxy]-2,3-dihydro-1H-isoindol-2-yl}pyridine-3-carbonitrile;
4-(5-methoxy-2,3-dihydro-1H-isoindol-2-yl)pyrimidine-5-carbonitrile;
4-{5-[(5-methoxypyridin-2-yl)methoxy]-2,3-dihydro-1H-isoindol-2-yl}pyrimidine-5-carbonitrile;
4-{5-[(5-hydroxypyridin-2-yl)methoxy]-2,3-dihydro-1H-isoindol-2-yl}pyridine-3-carbonitrile;
4-(5-methoxy-2,3-dihydro-1H-isoindol-2-yl)pyridine-3-carbonitrile; and
4-[5-(pyrimidin-5-ylmethoxy)-2,3-dihydro-1H-isoindol-2-yl]pyridine-3-carbonitrile;

or a pharmaceutically acceptable salt thereof, wherein the compound of Formula I, or a pharmaceutically acceptable salt there of, is labeled with one or more positron-emitting radionuclides.

Also provided is an imaging agent comprising a compound of Formula I is chosen from 2-(5-methoxy-2,3-dihydro-1H-isoindol-2-yl)pyridine-3-carbonitrile;
2-{5-[(5-methoxypyridin-2-yl)methoxy]-2,3-dihydro-1H-isoindol-2-yl}pyridine-3-carbonitrile;
2-[5-(pyrimidin-5-ylmethoxy)-2,3-dihydro-1H-isoindol-2-yl]pyridine-3-carbonitrile;
4-{5-[(5-methoxypyridin-2-yl)methoxy]-2,3-dihydro-1H-isoindol-2-yl}pyridine-3-carbonitrile;
4-(5-methoxy-2,3-dihydro-1H-isoindol-2-yl)pyrimidine-5-carbonitrile;
4-{5-[(5-methoxypyridin-2-yl)methoxy]-2,3-dihydro-1H-isoindol-2-yl}pyrimidine-5-carbonitrile;
4-{5-[(5-hydroxypyridin-2-yl)methoxy]-2,3-dihydro-1H-isoindol-2-yl}pyridine-3-carbonitrile;
4-(5-methoxy-2,3-dihydro-1H-isoindol-2-yl)pyridine-3-carbonitrile;
4-[5-(pyrimidin-5-ylmethoxy)-2,3-dihydro-1H-isoindol-2-yl]pyridine-3-carbonitrile;
5-[(5-methoxypyrazin-2-yl)methoxy]-2-(pyridin-4-yl)-2,3-dihydro-1H-isoindole;
4-[5-(benzyloxy)-2,3-dihydro-1H-isoindol-2-yl]pyrimidine-5-carbonitrile;
4-{5-[(5-hydroxypyridin-2-yl)methoxy]-2,3-dihydro-1H-isoindol-2-yl}pyrimidine-5-carbonitrile;
6-{5-[(5-methoxypyridin-2-yl)methoxy]-2,3-dihydro-1H-isoindol-2-yl}-2-methyl-2,3-dihydropyridazin-3-one; and
5-[(5-methoxypyridin-2-yl)methoxy]-2-(pyridin-4-yl)-2,3-dihydro-1H-isoindol-1-one, or a pharmaceutically acceptable salt thereof, wherein the compound of Formula I, or a pharmaceutically acceptable salt there of, is labeled with one or more positron-emitting radionuclides.

The compounds of Formula I, or a pharmaceutically acceptable salt thereof are labeled with one or more positron-emitting radionuclides. Suitable positron-emitting radionuclides that may be incorporated in the compounds of described herein, but are not limited to, $^{11}C$, $^{13}N$, $^{15}O$, $^{18}F$, $^{52}Fe$, $^{62}Cu$, $^{64}Cu$, $^{68}Ga$, $^{74}As$, $^{82}Rb$, $^{89}Zr$, $^{122}I$ and $^{124}I$.

In some embodiments, the one or more positron-emitting radionuclides are selected from: $^{11}C$, $^{13}N$, $^{15}O$, $^{18}F$, $^{76}Br$, and $^{124}I$. In some embodiments the one or more positron-emitting radionuclides are selected from $^{11}C$, $^{13}N$, $^{15}O$, and $^{18}F$.

Non-metal radionuclides may be covalently linked to the compounds described herein by a reaction well known from the state of art. When the radionuclide is a metallic positron-emitter, it is understood that labeling may require the use of a chelating agent. Such chelating agents are well known from the state of the art.

A PET imaging agent may be labelled with the positron emitter $^{11}C$ or $^{18}F$. Methods for the introduction of $^{11}C$ may include, but are not limited to, alkylation with [$^{11}C$]iodomethane or [$^{11}C$]methyl triflate. Carbon-11 has a half-life of approximately 20 minutes, thus $^{11}C$ needs to be generated in an on-site cyclotron, and is generally produced as [$^{11}C$] carbon dioxide. The [$^{11}C$]carbon dioxide is converted to the chemical species appropriate for the radiosynthesis (generally [$^{11}C$]iodomethane or the like), and the synthesis of the radiopharmaceutical is completed and used on-site in a PET imaging study after the appropriate radiochemical purity and specific activity have been determined. Typical methods of introducing $^{18}F$ may include but are not limited to displacement of a halide, tosylate, or other leaving group with [$^{18}F$]tetrabutylamonium fluoride or [$^{18}F$]potassium fluoride kryptofix-222. Fluorine-18 has a half life of approximately 110 minutes, thus synthesis of [$^{18}$F]radiopharmaceuticals need not necessarily have to occur at the site of the cyclotron nor proximal to the PET imaging study center. General methods for the introduction of these positron emitters are described in the literature (Miller et al., *Angewandte Chemie International Edition*, 47 (2008), 8998-9033).

Provided are methods of generating diagnostic images in an individual comprising administering an effective amount of an imaging agent described herein to an individual, and generating an image of at least a part of the individual.

Also provided are methods of generating diagnostic images in a biological sample comprising contacting the biological sample with an effective amount of an imaging agent described herein and generating an image of the positron-emitter labeled compound associated with the biological sample. In this method both the contacting and the generating may be conducted in vitro, alternatively the contacting is in vivo and the generating in vitro.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the brain of the individual; and detecting the presence or absence of the pathologic process. In some embodiments, the HTT protein aggregates are present in the basal ganglia of the brain of the individual. In some embodiments, the pathologic process is Huntington's disease (HD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are diagnostic methods of using the imaging agents to monitor disease progression in a patient by quantifying the change in levels of the target aggregates in the patient.

Also provided are methods for detecting the presence or absence of a neurodegenerative pathologic process associated with huntingtin protein (HTT protein) in an individual comprising: administering an effective amount of a positron-emitter labeled compound described herein; generating an image to detect the presence or absence of HTT protein aggregates in the individual; and detecting the presence or absence of the pathologic process. In some embodiments, the HTT protein monomers or aggegates are present in the brain, liver, heart, or muscle of said individual. In some embodiments, the HTT protein aggregates are present in the basal ganglia, cortex, hippocampus, or brain stem of the brain of the individual. In some embodiments, the pathologic process is Huntington's disease (HD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Also provided are methods for detecting the presence or absence of a neurodegenerative pathologic process associated with β-amyloid protein in an individual comprising: administering an effective amount of a positron-emitter labeled compound described herein; generating an image to detect the presence or absence of β-amyloid protein aggregates in the individual; and detecting the presence or absence of the pathologic process. In some embodiments, the β-amyloid protein monomers or aggegates are present in the brain, liver, heart, or muscle of said individual. In some embodiments, the β-amyloid protein aggregates are present in the basal ganglia, cortex, hippocampus, or brain stem of the brain of the individual. In some embodiments, the pathologic process is Alzheimer's Disease (AD). In some embodiments, the effective amount of the imaging agent comprises from about 0.1 to about 20 mCi. In some embodiments, the effective amount of the imaging agent comprises about 10 mCi. In some embodiments, generating an image comprises positron emission tomography (PET) imaging, PET with concurrent computed tomography imaging (PET/CT), PET with concurrent magnetic resonance imaging (PET/MRI), or a combination thereof. In some embodiments, generating an image comprises PET imaging.

Provided herein are compounds having suitable HTT protein aggregate or β-amyloid protein aggregate binding kinetics to function as efficient imaging agents for HTT protein aggregates or β-amyloid protein aggregates. The requirements of the compounds of the invention to function as efficient imaging agents for HTT protein aggregates are: 1) a high affinity for HTT protein aggregates; 2) a low affinity for nearby structures; 3) slow dissociation kinetics from HTT protein aggregates, which may conveniently be expressed as the dissociation rate constant $k_{diss}$ as defined in the following equation, wherein A and B refer to the HTT protein aggregate and the imaging agent, and $k_{assn}$ is the association rate constant.

$$d[AB]/dt = k_{assn}[A][B] - k_{diss}[AB]$$

The part of the brain most affected by HD, and thus most likely to contain HTT protein abnormalities, is a group of nerve cells at the base of the brain known collectively as the basal ganglia. The basal ganglia organize muscle-driven movements of the body, or "motor movement." The major components of the basal ganglia are the caudate and the putamen (together known as the striatum) and the globus pallidus (external and internal regions). The substantia nigra and the subthalamic nucleus are often included as part of the basal ganglia as well.

The term basal ganglia, refers to a group of subcortical nuclei responsible primarily for motor control, as well as other roles such as motor learning, executive functions and behaviors, and emotions. Disruption of the basal ganglia network forms the basis for several movement disorders. Normal function of the basal ganglia requires fine tuning of neuronal excitability within each nucleus to determine the exact degree of movement facilitation or inhibition at any given moment. This is mediated by the complex organization of the striatum, where the excitability of medium spiny neurons is controlled by several pre- and postsynaptic mechanisms as well as interneuron activity, and secured by several recurrent or internal basal ganglia circuits. The motor circuit of the basal ganglia has two entry points, the striatum and the subthalamic nucleus, and an output, the globus pallidus pars interna, which connects to the cortex via the motor thalamus.

Provided are methods for imaging part of the brain of an individual involving administering a positron-emitter labeled compound described herein to the individual, e.g. into the individual's vascular system, from where it passes through the blood-brain barrier, and then generating an image of at least the part of the individual's brain to which the compound has distributed.

Also provided are pharmaceutical compositions comprising an effective amount of a positron-emitter labeled compound described herein, or a pharmaceutically acceptable salt thereof, together with one or more pharmaceutically-acceptable adjuvants, excipients or diluents.

An imaging agent or pharmaceutical composition thereof may be administered to a patient in need of treatment via any suitable route. Routes of administration may include, for example, parenteral administration (including subcutaneous, intramuscular, intravenous, by means of, for example a drip patch). Further suitable routes of administration include (but are not limited to) oral, rectal, nasal, topical (including buccal and sublingual), infusion, vaginal, intradermal, intraperitoneally, intracranially, intrathecal and epidural administration or administration via oral or nasal inhalation, by means of, for example a nebulizer or inhaler, or by an implant.

An imaging agent or pharmaceutical composition thereof may also be administered via microspheres, liposomes, other microparticulate delivery systems or sustained release formulations placed in certain tissues including blood. Suitable examples of sustained release carriers include semi-permeable polymer matrices in the form of shared articles, e.g., suppositories or microcapsules. Examples of the techniques and protocols mentioned above and other techniques and protocols which may be used in accordance with the invention can be found in Remington's Pharmaceutical Sciences, 18th edition, Gennaro, A. R., Lippincott Williams & Wilkins; 20th edition (Dec. 15, 2000) ISBN 0-912734-04-3 and Pharmaceutical Dosage Forms and Drug Delivery Systems; Ansel, N. C. et al. 7th Edition ISBN 0-683305-72-7, the entire disclosures of which are herein incorporated by reference.

Also provided are uses of positron-emitter labeled compounds described herein for the manufacture of an imaging agent for use in a method of diagnosis of an individual.

Provided are methods of generating diagnostic images comprising proton emission tomography (PET). PET involves the administration of a positron-emitting radionuclide tracer to an individual. Once the tracer has had sufficient time to associate with the target of interest, the individual is placed within in a scanning device comprising a ring of scintillation detectors. An emitted positron travels through the individual's tissue for a short (isotope-dependent) distance, until it interacts with an electron. The interaction annihilates both the electron and the positron, producing a pair of photons moving in approximately opposite directions. These are detected when they reach a scintillator in the scanning device. Photons that do not arrive in pairs are ignored.

Also provided are methods of generating diagnostic images comprising PET with concurrent computed tomography imaging (PET/CT), or with concurrent magnetic resonance imaging (PET/MRI). Computed tomography uses X-rays to show the structure of the brain, while magnetic resonance imaging uses magnetic fields and radio waves.

Other uses of the disclosed imaging agents and methods will become apparent to those skilled in the art based upon, inter alia, a review of this disclosure.

As will be recognized, the steps of the methods described herein need not be performed any particular number of times or in any particular sequence. Additional objects, advantages and novel features of the disclosure will become apparent to those skilled in the art upon examination of the following examples thereof, which are intended to be illustrative and not intended to be limiting.

EXAMPLES

General Experimental Details

Commercially available reagents and solvents (HPLC grade) were used without further purification. $^1$H NMR spectra were recorded on a Bruker DRX 500 MHz spectrometer or a Bruker DPX 250 MHz spectrometer in deuterated solvents. Chemical shifts (δ) are in parts per million. SCX chromatography was performed with Biotage Isolute Flash SCX-2 loading the sample in methanol and eluting with methanol then 5% ammonia in methanol.

Analytical HPLC-MS (METCR1278), was performed on Shimadzu LCMS-2010EV systems using reverse phase Atlantis dC18 columns (3 μm, 2.1×50 mm), gradient 5-100% B (A=water/0.1% formic acid, B=acetonitrile/0.1% formic acid) over 3 minutes injection volume 3 μL, flow=1.0 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (METCR1416) analytical HPLC-MS on Shimadzu LCMS-2010EV systems using reverse phase Water Atlantis dC18 columns (3 μm, 2.1×100 mm), gradient 5-100% B (A=water/0.1% formic acid, B=acetonitrile/0.1% formic acid) over 7 minutes, injection volume 3 μL, flow=0.6 mL/minute. UV spectra were recorded at 215 nm using a SPD-M20A photo diode array detector. Mass spectra were obtained over the range m/z 150 to 850 at a sampling rate of 2 scans per second using a LCMS2010EV. Data were integrated and reported using Shimadzu LCMS-Solutions and PsiPort software.

Alternatively, (MET-uHPLC-AB-101) analytical HPLC-MS were performed on a Waters Acquity UPLC system with Waters PDA and ELS detectors using a Phenomenex Kinetex-XB C-18 column, (1.7 μM, 2.1 mm×100 mm at a column temperature of 40° C., gradient 5-100% B (A=water/0.1% formic acid; B=acetonitrile/0.1% formic acid) over 5.3 minutes, then 100% B for 0.5 minute, flow=0.6 mL/minute. UV spectra were recorded at 215 nm using a Waters Acquity photo diode array. Mass spectra were obtained over the range m/z 150 to 850 at a sampling rate of 5 scans per second using a Waters SQD. Data were integrated and reported using Waters MassLynx and OpenLynx software.

All example compounds display an LC purity of >95% unless stated otherwise.

Method 1

Scheme for Method 1

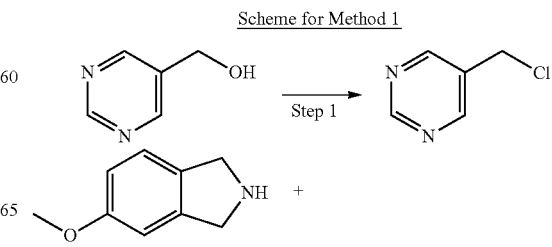

-continued

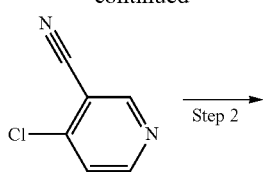

Step 1, Method 1: 5-(chloromethyl)pyrimidine hydrochloride

To a solution of pyrimidin-5-ylmethanol (48 mg, 0.43 mmol) in dichloromethane (3 mL), thionyl dichloride (0.26 mL, 3.6 mmol) was added drop-wise at 0° C. The mixture was heated to reflux for 2 hours, then the mixture was concentrated. Dichloromethane (5 mL) was added and the mixture was concentrated (×3) to give the title compound as a yellow oil which was used directly in the next step. Tr(METCR1278)=0.90 min, (ES$^+$) (M+H)$^+$129/131.

Step 2, Method 1: 4-(5-Methoxy-2,3-dihydro-1H-isoindol-2-yl)pyridine-3-carbonitrile 5-Methoxy-2,3-dihydro-1H-isoindole hydrochloride (500 mg, 2.69 mmol), 4-chloropyridine-3-carbonitrile (448 mg, 3.23 mmol) and diisopropylethylamine (1.4 mL, 8.08 mmol) were suspended in n-butanol (6 mL). The reaction was heated in a microwave at 140° C. for 1 hour. The reaction mixture was partitioned between ethyl acetate (50 mL) and water (30 mL) and the aqueous was extracted with ethyl acetate (2×30 mL). The combined organic extracts were washed with brine (15 mL), dried over anhydrous sodium sulphate, filtered and concentrated. Purification by FCC (silica, 20-100% ethyl acetate in heptane) gave the title compound 230 mg (34% yield) as an off white solid. Tr(METCR1278)=1.28 min, (ES$^+$) (M+H)$^+$252.

Step 3, Method 1: 4-(5-Hydroxy-2,3-dihydro-1H-isoindol-2-yl)pyridine-3-carbonitrile 4-(5-Methoxy-2,3-dihydro-1H-isoindol-2-yl)pyridine-3-carbonitrile (230 mg, 0.92 mmol) was dissolved in dichloromethane (15 mL) and stirred in a nitrogen atmosphere. The reaction mixture was cooled to 0° C. and 1 M boron tribromide in dichloromethane (4.58 mL, 4.58 mmol) was added slowly. The reaction mixture was allowed to warm to room temperature and was stirred for 48 hours. The reaction mixture was cooled to 0° C. and methanol (20 mL) was added slowly. The solvents were removed in vacuo to give the title compound 313 mg (quantitative yield) as a beige solid. Tr(METCR1278)=1.36 min, (ES$^+$) (M+H)$^+$238, 90%.

Step 4, Method 1: 4-[5-(Pyrimidin-5-ylmethoxy)-2,3-dihydro-1H-isoindol-2-yl]pyridine-3-carbonitrile 4-(5-Hydroxy-2,3-dihydro-1H-isoindol-2-yl)pyridine-3-carbonitrile (90%, 313 mg, 1.19 mmol), 5-(chloromethyl)pyrimidine hydrochloride (crude 1.42 mmol) and potassium iodide (217 mg, 1.31 mmol) were dissolved in anhydrous N,N-dimethylformamide (3 mL) and stirred for 5 minutes at room temperature. Sodium hydride (60% in mineral oil, 142 mg, 3.56 mmol) was added and the reaction mixture was stirred at room temperature for 24 hours. Water (0.1 mL) was added and the solvents were removed in vacuo. The residue was partitioned between ethyl acetate (50 mL) and water (50 mL) and the aqueous phase was extracted with ethyl acetate (2×50 mL). The combined organic extracts were washed with water (20 mL), brine (20 mL), dried over anhydrous sodium sulphate, filtered and concentrated. Purification by preparative HPLC (acetonitrile-water-0.2% ammonium hydroxide) gave the title compound 19.5 mg (5% yield) as an off white solid.

Example 1, Method 1: 4-[5-(Pyrimidin-5-ylmethoxy)-2,3-dihydro-1H-isoindol-2-yl]pyridine-3-carbonitrile $\delta_H$ NMR (500 MHz, DMSO) 9.19 (s, 1H), 8.93 (s, 2H), 8.51 (s, 1H), 8.29 (d, J=6.3 Hz, 1H), 7.37 (d, J=8.4 Hz, 1H), 7.16 (d, J=1.9 Hz, 1H), 7.05 (dd, J=8.4, 2.3 Hz, 1H), 6.77 (d, J=6.3 Hz, 1H), 5.23 (s, 2H), 5.03 (s, 2H), 4.97 (s, 2H). Tr(MET-uHPLC-AB-101)=1.4 min, (ES$^+$) (M+H)$^+$330.

The following examples were prepared using Method 1 described above:

TABLE 1

| Ex. | Structure | Mol. Weight | IUPAC Name | LCMS data |
|---|---|---|---|---|
| 1 | 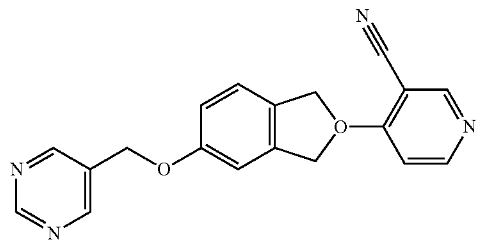 | 329.36 | 4-[5-(Pyrimidin-5-ylmethoxy)-2,3-dihydro-1H-isoindol-2-yl]pyridine-3-carbonitrile | Tr(MET-uHPLC-AB-101) = 1.4 min, (ES$^+$) (M + H)$^+$ 330 |
| 2 | 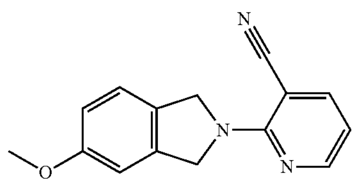 [SMILES: COc1ccc2c(c1)CN(c1ncccc1C#N)C2] | 251.28 | 2-(5-Methoxy-2,3-dihydro-1H-isoindol-2-yl)pyridine-3-carbonitrile | Tr(MET-uHPLC-AB-101) = 3.42 min, (ES$^+$) (M + H)$^+$ 252 |
| 3 | 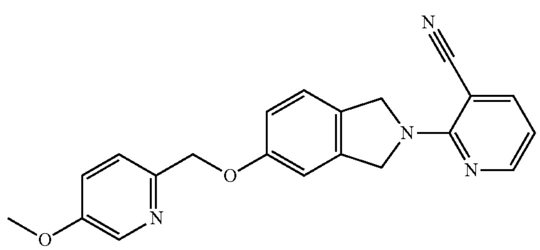 [SMILES: COc1ccc(COc2ccc3c(c2)CN(c2ncccc2C#N)C3)nc1] | 358.39 | 2-{5-[(5-Methoxypyridin-2-yl)methoxy]-2,3-dihydro-1H-isoindol-2-yl}pyridine-3-carbonitrile | Tr(MET-uHPLC-AB-101) = 3.32 min, (ES$^+$) (M + H)$^+$ 359 |
| 4 | 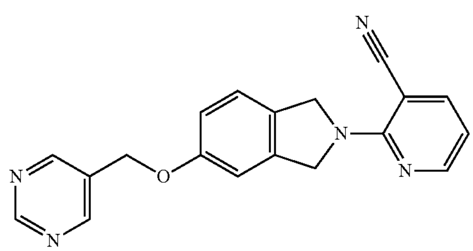 [SMILES: N#Cc1cccnc1N1Cc2ccc(OCc3cncnc3)cc2C1] | 329.36 | 2-[5-(Pyrimidin-5-ylmethoxy)-2,3-dihydro-1H-isoindol-2-yl]pyridine-3-carbonitrile | Tr(MET-uHPLC-AB-101) = 3.0 min, (ES$^+$) (M + H)$^+$ 330 |
| 5 | 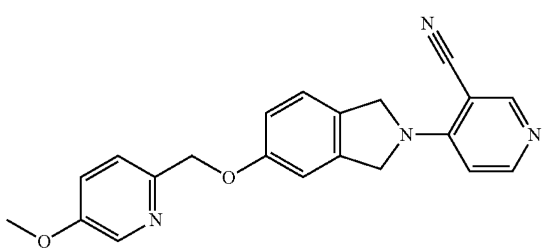 [SMILES: COc1ccc(COc2ccc3c(c2)CN(c2ccncc2C#N)C3)nc1] | 358.39 | 4-{5-[(5-Methoxypyridin-2-yl)methoxy]-2,3-dihydro-1H-isoindol-2-yl}pyridine-3-carbonitrile | Tr(MET-uHPLC-AB-101) = 1.7 min, (ES$^+$) (M + H)$^+$ 359 |
| 6 | 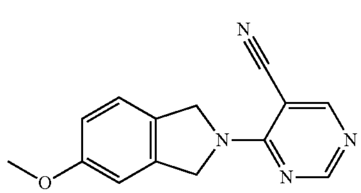 [SMILES: COc1ccc2c(c1)CN(c1ncncc1C#N)C2] | 252.27 | 4-(5-Methoxy-2,3-dihydro-1H-isoindol-2-yl)pyrimidine-5-carbonitrile | Tr(METCR1416) = 2.75 min, (ES$^+$) (M + H)$^+$ 253 |

TABLE 1-continued
| Ex. | Structure | Mol. Weight | IUPAC Name | LCMS data |
|---|---|---|---|---|
| 7 | 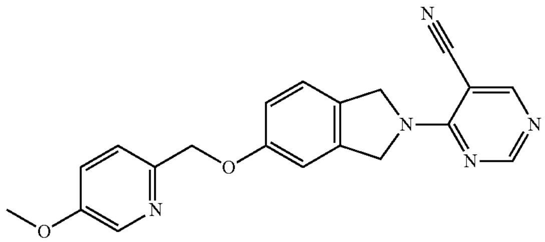 | 359.38 | 4-{5-[(5-Methoxypyridin-2-yl)methoxy]-2,3-dihydro-1H-isoindol-2-yl}pyrimidine-5-carbonitrile | Tr(MET-uHPLC-AB-101) = 2.76 min, (ES+) (M + H)+ 360 |
| 8 | 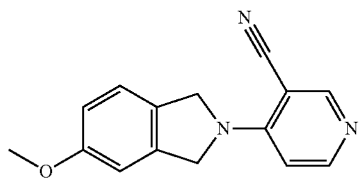 [SMILES: COc1ccc2c(c1)CN(c1ccncc1C#N)C2] | 251.28 | 4-(5-Methoxy-2,3-dihydro-1H-isoindol-2-yl)pyridine-3-carbonitrile | Tr(MET-uHPLC-AB-101) = 1.47 min, (ES+) (M + H)+ 252 |
| 9 | 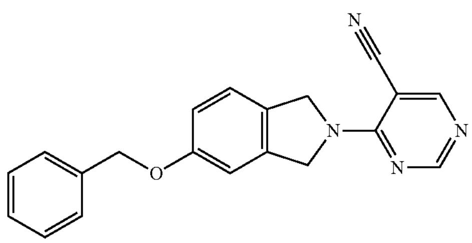 [SMILES: N#Cc1cncnc1N1Cc2ccc(OCc3ccccc3)cc2C1] | 328.38 | 4-[5-(Benzyloxy)-2,3-dihydro-1H-isoindol-2-yl]pyrimidine-5-carbonitrile | Tr(MET-uHPLC-AB-101) = 3.68 min, (ES+) (M + H)+ 329 |
Method 2
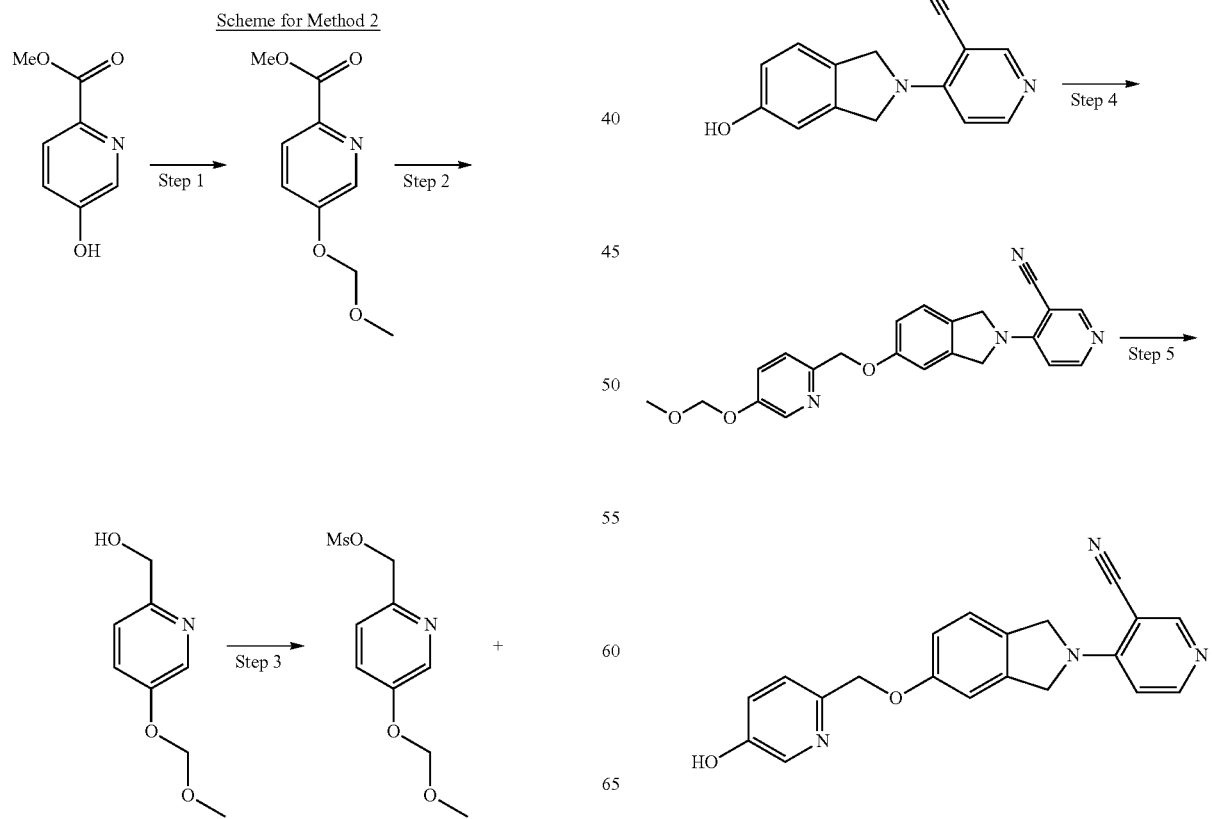

Step 1, Method 2: Methyl 5-(methoxymethoxy)pyridine-2-carboxylate

Sodium hydride (60% in mineral oil, 144 mg, 3.59 mmol) was suspended in anhydrous N,N-dimethylformamide (5 mL) and cooled to 0° C. Methyl 5-hydroxypyridine-2-carboxylate (500 mg, 3.27 mmol) dissolved in N,N-dimethylformamide (5 mL) was added slowly to the suspension. The reaction mixture was allowed to stir under nitrogen and warm to room temperature over 30 minutes. The reaction was cooled to 0° C. and chloro(methoxy)methane (0.26 mL, 3.43 mmol) was added drop-wise over 15 minutes. The reaction was allowed to warm to room temperature and stirred for 16 hours. Water (20 mL) was added and the solvents were removed in vacuo. The mixture was partitioned between ethyl acetate and water (1:1, 100 mL) and extracted with ethyl acetate (3×60 mL). The combined organic extracts were washed with water (3×80 mL), brine (50 mL), dried over anhydrous magnesium sulphate, filtered and concentrated to give the title compound 0.6 g (89% yield) as an orange oil which solidified upon standing. Tr(METCR1278)=1.33 min, (ES$^+$) (M+H)$^+$198.

Step 2, Method 2: [5-(Methoxymethoxy)pyridin-2-yl]methanol

Methyl 5-(methoxymethoxy)pyridine-2-carboxylate (0.39 g, 1.9 mmol) was dissolved in anhydrous tetrahydrofuran (15 mL) and cooled to 0° C. in a nitrogen atmosphere. 2.4 M lithium aluminium hydride in tetrahydrofuran (0.87 mL, 2.09 mmol) was added drop-wise over a period of 5 minutes, and the reaction was stirred at 0° C. for 1.5 hours. The reaction was cooled to 0° C. and saturated aqueous Rochelle's salt (1 mL) was added drop-wise with vigorous stirring over a period of 10 minutes. The reaction mixture was allowed to warm to room temperature for 1 hour. The resultant emulsion was filtered through glass fibre filter paper. The filter paper was washed with saturated aqueous sodium bicarbonate (10 mL), followed by ethyl acetate (3×10 mL). The phases were separated and the aqueous phase was extracted with ethyl acetate (3×10 mL). The combined organic extracts were washed with brine (10 mL), dried over sodium sulphate, filtered, and concentrated to give the title compound 276 mg (86% yield) as an orange oil. Tr(METCR1278)=1.09 min, (ES$^+$) (M+H)$^+$170.

Step 3, Method 2: [5-(Methoxymethoxy)pyridin-2-yl]methyl methanesulfonate

[5-(Methoxymethoxy)pyridin-2-yl]methanol (276 mg, 1.63 mmol) was dissolved in dichloromethane (5 mL), cooled to 0° C. and stirred in a nitrogen atmosphere. Triethylamine (250 µL, 1.79 mmol) was added, followed by drop-wise addition of methanesulfonyl chloride (133 µL, 1.71 mmol). The reaction was stirred for 45 minutes at 0° C. and allowed to warm to room temperature. Water (5 mL) was added and the phases separated. The aqueous layer was extracted with dichloromethane (3×15 mL); the combined organic extracts were washed with brine (10 mL), dried over anhydrous sodium sulphate, filtered, and concentrated to give the title compound, 275 mg (59% yield) as a dark red oil. Tr(METCR1278)=1.35 min, (ES$^+$) (M+H)$^+$248.

Step 4, Method 2: 4-(5-{[5-(Methoxymethoxy)pyridin-2-yl]methoxy}-2,3-dihydro-1H-isoindol-2-yl)pyridine-3-carbonitrile 4-(5-Hydroxy-2,3-dihydro-1H-isoindol-2-yl)pyridine-3-carbonitrile (330 mg, 1.66 mmol prepared by Method 1), [5-(methoxymethoxy)pyridin-2-yl]methyl methanesulfonate (532 mg, 1.66 mmol) and potassium iodide (62 mg, 0.37 mmol) were dissolved in anhydrous N,N-dimethylformamide (4 mL). Sodium hydride (60% in mineral oil, 27 mg, 0.16 mmol) was added and the mixture was stirred at room temperature for 44 hours. The reaction mixture was quenched with methanol (2 mL) and partitioned between ethyl acetate (100 mL), saturated aqueous sodium bicarbonate (50 mL) and brine (50 mL). After separation the aqueous layer was extracted with ethyl acetate (3×100 mL). The organic extracts were combined, washed with brine (30 mL), dried over sodium sulphate and concentrated. The residue was triturated with ethyl acetate:heptane (1:1) to give the title compound 269 mg (39% yield) as a brown solid. $\delta_H$ NMR (500 MHz, DMSO) 8.49 (s, 1H), 8.33 (d, J=2.6 Hz, 1H), 8.27 (d, J=6.3 Hz, 1H), 7.49 (d, J=2.7 Hz, 1H), 7.48 (s, 1H), 7.32 (d, J=8.4 Hz, 1H), 7.09 (d, J=1.9 Hz, 1H), 6.98 (dd, J=8.4, 2.3 Hz, 1H), 6.74 (d, J=6.3 Hz, 1H), 5.26 (s, 2H), 5.12 (s, 2H), 4.96 (d, J=22.4 Hz, 4H), 3.38 (s, 3H).

Step 5, Method 2: 4-{5-[(5-Hydroxypyridin-2-yl)methoxy]-2,3-dihydro-1H-isoindol-2-yl}pyridine-3-carbonitrile To a solution of 4-(5-{[5-(methoxymethoxy)pyridin-2-yl]methoxy}-2,3-dihydro-1H-isoindol-2-yl)pyridine-3-carbonitrile (269 mg, 0.69 mmol) in tetrahydrofuran (40 mL) was added 3 M hydrochloric acid (4.6 mL) and the mixture was stirred at 60° C. for 8 hours. The mixture was stirred overnight at room temperature. The volatiles were removed in vacuo and the remaining residue was diluted with water. Solid sodium bicarbonate was added portion-wise until the pH was approximately 8. The solid was collected by filtration, washed with water (2×10 mL) and dried under vacuum. Purification by FCC (silica, 0-60% tetrahydrofuran in heptane) gave the title compound 101 mg (42% yield) as a white solid.

Example 4, Method 2: 4-{5-[(5-Hydroxypyridin-2-yl)methoxy]-2,3-dihydro-1H-isoindol-2-yl}pyridine-3-carbonitrile $\delta_H$ NMR (500 MHz, DMSO) 10.01 (s, 1H), 8.49 (s, 1H), 8.27 (d, J=6.3 Hz, 1H), 8.11 (d, J=2.5 Hz, 1H), 7.34 (d, J=8.4 Hz, 1H), 7.32 (d, J=8.4 Hz, 1H), 7.18 (dd, J=8.4, 2.9 Hz, 1H), 7.08 (d, J=2.0 Hz, 1H), 6.97 (dd, J=8.4, 2.4 Hz, 1H), 6.75 (d, J=6.3 Hz, 1H), 5.05 (s, 2H), 4.98 (s, 2H), 4.94 (s, 2H). Tr(MET-uHPLC-AB-101)=1.28 min, (ES$^+$) (M+H)$^+$ 345.

The following examples were prepared using Method 2 described above:

TABLE 2

| Ex. | Structure | Mol. Weight | IUPAC Name | LCMS data |
|---|---|---|---|---|
| 1 | 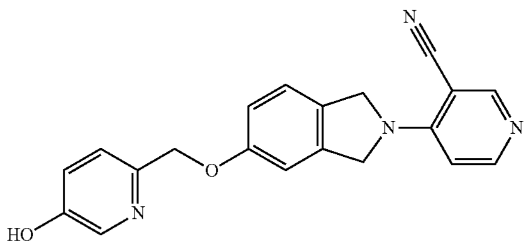 [SMILES: N#Cc1cnccc1N1Cc2ccc(OCc3ccc(O)cn3)cc2C1] | 344.37 | 4-{5-[(5-Hydroxypyridin-2-yl)methoxy]-2,3-dihydro-1H-isoindol-2-yl}pyridine-3-carbonitrile | Tr(MET-uHPLC-AB-101) = 1.28 min, (ES+) (M + H)+ 345 |
| 2 | 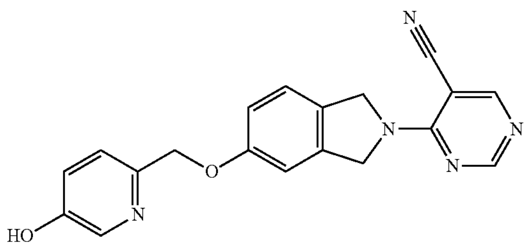 [SMILES: N#Cc1cncnc1N1Cc2ccc(OCc3ccc(O)cn3)cc2C1] | 345.36 | 4-{5-[(5-Hydroxypyridin-2-yl)methoxy]-2,3-dihydro-1H-isoindol-2-yl}pyrimidine-5-carbonitrile | Tr(MET-uHPLC-AB-101) = 2.02 min, (ES+) (M + H)+ 346 |

Method 3

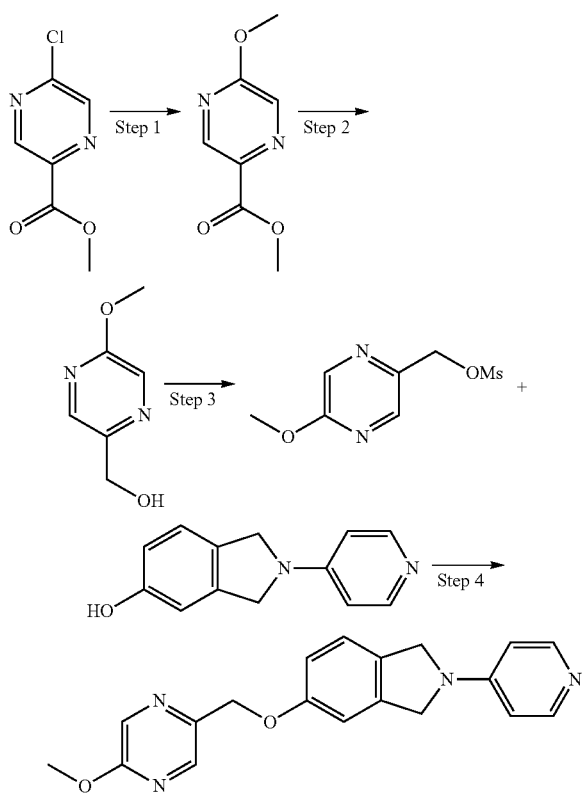

Scheme for Method 3

Step 1, Method 3: Methyl 5-methoxypyrazine-2-carboxylate

To methyl 5-chloropyrazine-2-carboxylate (2.00 g, 11.6 mmol) under nitrogen, was added a 0.5 M solution of sodium methoxide in methanol (27.8 mL, 13.9 mmol). The mixture was refluxed at 90° C. for 15 minutes. The mixture was then dissolved with water (80 mL) and extracted with ethyl acetate (2×100 mL). The combined organic extracts were dried over sodium sulphate, filtered and concentrated to give the title compound 1.68 g (79% yield) as a white powder. $\delta_H$ NMR (500 MHz, Chloroform) 8.88 (d, J=1.2 Hz, 1H), 8.28 (d, J=1.2 Hz, 1H), 4.05 (s, 3H), 4.00 (s, 3H). Tr(METCR1278)=1.23 min, (ES+) (M+H)+169.

Step 2, Method 3: (5-Methoxypyrazin-2-yl)methanol

Sodium borohydride (270 mg, 7.14 mmol) was added to a stirred solution of methyl 5-methoxypyrazine-2-carboxylate (200 mg, 1.19 mmol) in anhydrous tetrahydrofuran (8 mL) under nitrogen. The mixture was refluxed at 65° C. for 15 minutes, after which methanol (1.59 mL, 39.2 mmol) was added slowly. The reaction was refluxed at 65° C. for 1.5 hours. The mixture was quenched with water (0.5 mL), then diluted with further water (15 mL), extracted with ethyl acetate (2×25 mL) then 20% 2-propanol in dichloromethane (25 mL). The combined organic extracts were dried over sodium sulphate, filtered and concentrated to give the title compound 115 mg (69% yield) as a white crystalline solid. $\delta_H$ NMR (500 MHz, DMSO) 8.28-8.16 (m, 2H), 5.41 (t, J=5.8 Hz, 1H), 4.54 (d, J=5.6 Hz, 2H), 3.90 (s, 3H). Tr(METCR1278)=0.74 min, (ES+) (M+H)+141.

Step 3, Method 3: (5-Methoxypyrazin-2-yl)methyl methanesulfonate

To a stirred solution of (5-methoxypyrazin-2-yl)methanol (73 mg, 0.52 mmol) in dichloromethane (1 mL) under nitrogen, was added triethylamine (0.08 mL, 0.73 mmol) followed by methanesulfonyl chloride (0.042 mL, 0.55 mmol). The mixture was stirred at room temperature for 1 hour. The mixture was then partitioned between dichloromethane (10 mL) and water (10 mL). The organic extract was dried over sodium sulphate, filtered and concentrated to afford the title compound 59 mg (52% yield) as a yellow oil. Tr(METCR1278)=1.25 min, (ES$^+$) (M+H)$^+$219.

Step 4, Method 3: 5-[(5-Methoxypyrazin-2-yl)methoxy]-2-(pyridin-4-yl)-2,3-dihydro-1H-isoindole 2-(Pyridin-4-yl)-2,3-dihydro-1H-isoindol-5-ol (87%, 289 mg, 1.18 mmol, prepared by Method 1), (5-methoxypyrazin-2-yl)methyl methanesulfonate (310 mg, 1.42 mmol) and potassium iodide (197 mg, 1.18 mmol) were dissolved in anhydrous ALV-dimethylformamide (5 mL) and stirred for 5 minutes at room temperature. Sodium hydride (60% in mineral oil, 142 mg, 3.55 mmol) was added and the reaction mixture was stirred at room temperature under a nitrogen atmosphere for 40 hours. The solvents were removed in vacuo and purification by preparative HPLC (acetonitrile-water-0.2% ammonium hydroxide) gave the title compound, 30.1 mg (8% yield) as a beige solid.

Example 1, Method 3: 5-[(5-Methoxypyrazin-2-yl)methoxy]-2-(pyridin-4-yl)-2,3-dihydro-1H-isoindole $\delta_H$ NMR (500 MHz, DMSO) 8.38 (d, J=1.1 Hz, 1H), 8.34 (d, J=1.3 Hz, 1H), 8.17 (d, J=6.3 Hz, 2H), 7.32 (d, J=8.3 Hz, 1H), 7.10 (d, J=2.0 Hz, 1H), 7.01 (dd, J=8.4, 2.3 Hz, 1H), 6.57 (d, J=6.4 Hz, 2H), 5.17 (s, 2H), 4.62 (s, 2H), 4.58 (s, 2H), 3.92 (s, 3H). Tr(MET-uHPLC-AB-101)=1.77 min, (ES$^+$) (M+H)$^+$335.

The following example was prepared using Method 3 described above:

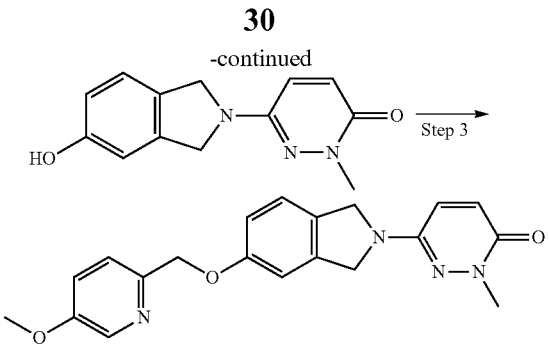

Step 1, Method 4: 6-(5-Methoxy-2,3-dihydro-1H-isoindol-2-yl)-2-methyl-2,3-dihydropyridazin-3-one 5-Methoxy-2,3-dihydro-1H-isoindole hydrochloride (170 mg, 0.92 mmol), 6-bromo-2-methyl-2,3-dihydropyridazin-3-one (182 mg, 0.96 mmol) and dicaesium carbonate (895.06 mg, 2.75 mmol) were suspended in anhydrous toluene (3 mL) and sonicated under a flow of nitrogen for 5 minutes. Palladium(II) acetate (20.56 mg, 0.09 mmol) and 4,5-Bis(diphenylphosphino)-9,9-dimethylxanthene (53 mg, 0.09 mmol) were added and the reaction was heated to 100° C. for 16 hours. The reaction mixture was cooled to room temperature and filtered through celite. The celite was washed with 10% methanol in dichloromethane and the filtrate was concentrated in vacuo and purified by FCC (silica, 20-100% ethyl acetate in heptane, 0-10% methanol in dichloromethane), SCX and HPLC (acetonitrile/water+ 0.2% formic acid) to give the title compound, 34 mg (14% yield) as a beige solid. $\delta_H$ NMR (500 MHz, DMSO) 7.30 (d, J=9.8 Hz, 1H), 7.27 (d, J=8.3 Hz, 1H), 6.96 (d, J=2.0 Hz,

TABLE 3

| Ex. | Structure | Mol. Weight | IUPAC Name | LCMS data |
| --- | --- | --- | --- | --- |
| 1 | 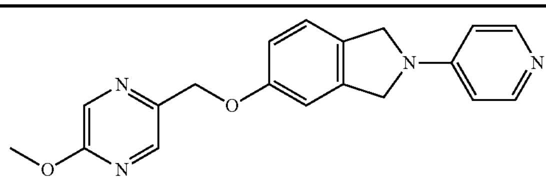 | 334.37 | 5-[(5-Methoxypyrazin-2-yl)methoxy]-2-(pyridin-4-yl)-2,3-dihydro-1H-isoindole | Tr(MET-uHPLC-AB-101) = 1.77 min, m/z (ES$^+$) (M + H)$^+$ 335 |

1H), 6.92-6.84 (m, 2H), 4.63 (s, 2H), 4.59 (s, 2H), 3.76 (s, 3H), 3.53 (s, 3H). Tr(MET-uHPLC-AB-101)=2.56 min, (ES$^+$) (M+H)$^+$258.

Step 2, Method 4: 6-(5-Hydroxy-2,3-dihydro-1H-isoindol-2-yl)-2-methyl-2,3-dihydropyridazin-3-one 6-(5-Methoxy-2,3-dihydro-1H-isoindol-2-yl)-2-methyl-2,3-dihydropyridazin-3-one (96 mg, 0.37 mmol) was dissolved in anhydrous dichloromethane (5 mL) and 1 M tribromoborane in dichloromethane (0.6 mL) was added and the reaction was stirred at room temperature for 16 hours. 1 M tribromoborane in dichloromethane (0.2 mL) was added and the reaction was stirred at room temperature for 2 hours. Saturated sodium bicarbonate solution (15 mL) was added and the reaction mixture was stirred vigorously for 20 minutes. The reaction mixture was filtered and the precipitate was co-distilled from methanol (5 mL) and toluene Method 4

Scheme for Method 4

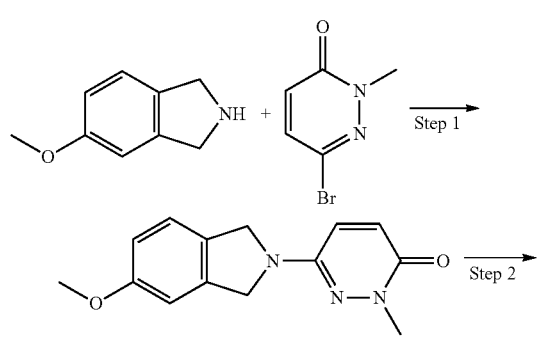

(2×10 mL) to give the title compound, 84 mg (90% yield) as a beige solid. δ$_H$ NMR (500 MHz, DMSO) 7.29 (d, J=9.8 Hz, 1H), 7.14 (d, J=8.2 Hz, 1H), 6.88 (d, J=9.8 Hz, 1H), 6.75 (s, 1H), 6.69 (dd, J=8.2, 2.1 Hz, 1H), 4.58 (s, 2H), 4.55 (s, 2H), 3.52 (s, 3H). Tr(METCR1673)=0.94 min, (ES$^+$) (M$^+$H)$^+$244.

Step 3, Method 4: 6-{5-[(5-Methoxypyridin-2-yl)methoxy]-2,3-dihydro-1H-isoindol-2-yl}-2-methyl-2,3-dihydropyridazin-3-one (5-Methoxypyridin-2-yl)methanol (54 mg, 0.37 mmol) was dissolved in anhydrous dichloromethane (3 mL), thionyl dichloride (0.25 ml, 3.35 mmol) was added and the reaction was heated to 50° C. in a nitrogen atmosphere for 2 hours. The reaction mixture was cooled to room temperature, concentrated in vacuo from dichloromethane (3×10 mL), to give a brown oil which was used crude in the subsequent step. 6-(5-Hydroxy-2,3-dihydro-1H-isoindol-2-yl)-2-methyl-2,3-dihydropyridazin-3-one (97%, 84 mg, 0.33 mmol), potassium iodide (61 mg, 0.37 mmol) and 2-(chloromethyl)-5-methoxypyridine (58 mg, 0.37 mmol) were dissolved in anhydrous N,N-dimethylformamide (5 mL), sodium hydride (60%, 40.19 mg, 1 mmol) was added and the reaction was stirred for 1 hour at room temperature in a nitrogen atmosphere. Sodium hydride (60%, 40 mg, 1 mmol) was added and the reaction was heated to 70° C. for 3 hours. The reaction mixture was cooled to room temperature, quenched with the addition of water (1 mL) and the solvents were removed in vacuo and the stood for 16 hours. The residue was partitioned between ethyl acetate (50 mL) and water (50 mL), the phases were separated and the aqueous layer was further extracted with ethyl acetate (2×50 mL), the combined organics were washed with brine (10 mL), dried over anhydrous magnesium sulfate, filtered, and the filtrate was evaporated in vacuo. Purification by FCC (silica, 20-100% ethyl acetate in heptane, 10% methanol in dichloromethane) gave the title compound, 32 mg (26% yield) as a beige solid.

Example 1, Method 4: 6-{5-[(5-Methoxypyridin-2-yl)methoxy]-2,3-dihydro-1H-isoindol-2-yl}-2-methyl-2,3-dihydropyridazin-3-one δ$_H$ NMR (500 MHz, DMSO) 8.28 (d, J=2.8 Hz, 1H), 7.47 (d, J=8.6 Hz, 1H), 7.42 (dd, J=8.6, 2.9 Hz, 1H), 7.30 (d, J=9.8 Hz, 1H), 7.27 (d, J=8.4 Hz, 1H), 7.05 (d, J=2.0 Hz, 1H), 6.95 (dd, J=8.4, 2.3 Hz, 1H), 6.89 (d, J=9.8 Hz, 1H), 5.11 (s, 2H), 4.62 (s, 2H), 4.59 (s, 2H), 3.83 (s, 3H), 3.53 (s, 3H). Tr(MET-uHPLC-AB-101)=2.56 min, (ES$^+$) (M+H)$^+$ 365.

The following example was prepared using Method 4 described above:

Method 5

Scheme for Method 5

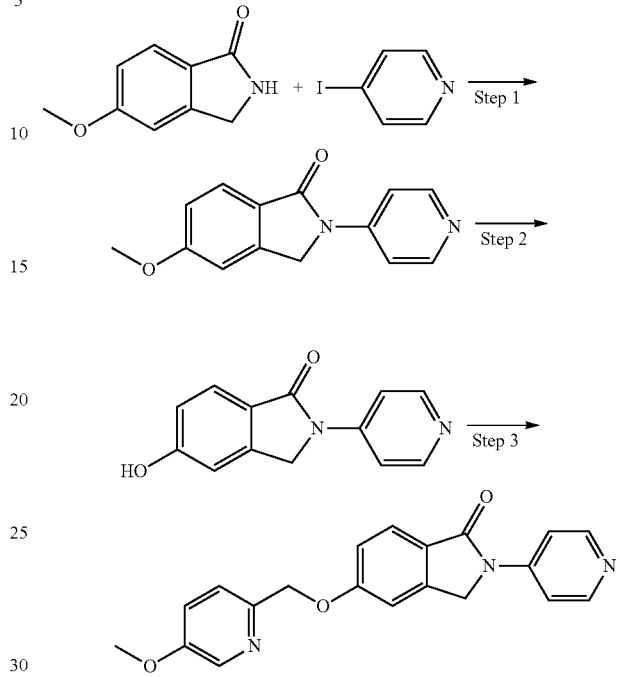

Step 1, Method 5: 5-Methoxy-2-(pyridin-4-yl)-2,3-dihydro-1H-isoindol-1-one

5-Methoxy-2,3-dihydro-1H-isoindol-1-one (100 mg, 0.61 mmol), 4-iodopyridine (126 mg, 0.61 mmol), (9,9-dimethyl-9H-xanthene-4,5-diyl)bis(diphenylphosphane) (53 mg, 0.09 mmol) and dicaesium carbonate (300 mg, 0.92 mmol) were suspended in dry dioxane (1 mL) and the mixture was degassed. (1E,4E)-1,5-Diphenylpenta-1,4-dien-3-one-palladium (3:2) (28 mg, 0.03 mmol) was added and the mixture heated in a microwave at 140° C. for 90 minutes. The mixture was diluted with ethyl acetate (10 mL) and water (5 mL) and filtered to give the title compound 28 mg (20% yield) as a brown powder. δ$_H$ NMR (500 MHz, DMSO) 8.58-8.47 (m, 2H), 7.91-7.82 (m, 2H), 7.74 (d, J=8.5 Hz, 1H), 7.23 (d, J=1.9 Hz, 1H), 7.11 (dd, J=8.5, 2.3 Hz, 1H), 4.98 (s, 2H), 3.89 (s, 3H). Tr(MET-uHPLC-AB-101)=1.27 min, (ES$^+$) (M+H)$^+$241.

TABLE 4

| Ex. | Structure | Mol. Weight | IUPAC Name | LCMS data |
|---|---|---|---|---|
| 1 | 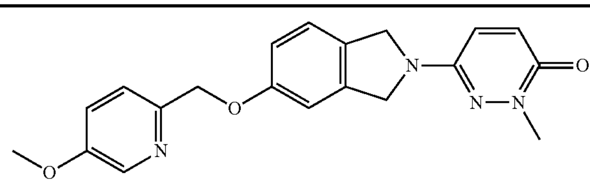 | 364.41 | 6-{5-[(5-Methoxypyridin-2-yl)methoxy]-2,3-dihydro-1H-isoindol-2-yl}-2-methyl-2,3-dihydropyridazin-3-one | Tr(MET-uHPLC-AB-101) = 2.56 min, m/z (ES$^+$) (M + H)$^+$ 365 |

Step 2, Method 5: 5-Hydroxy-2-(pyridin-4-yl)-2,3-dihydro-1H-isoindol-1-one

To 5-methoxy-2-(pyridin-4-yl)-2,3-dihydro-1H-isoindol-1-one (37 mg, 0.15 mmol in 1,2-dichloroethane (10 mL) was added tribromoborane 1 M in dichloromethane (1.54 mL 1.54 mmol) and the mixture heated to reflux overnight. Tribromoborane 1 M in dichloromethane (1.54 mL 1.54 mmol) and the mixture heated to reflux for 2 days the stood at room temperature for 2 days. The mixture was poured onto a 1:1 ice:saturate sodium bicarbonate mixture (50 mL) and stirred for 1 hour. The mixture was filtered and washed with water (5 mL) and dichloromethane then dried in a vacuum oven to give the title compound 19 mg (55% yield) as a tan powder. $\delta_H$ NMR (250 MHz, DMSO, 353 K) 8.72 (d, J=7.4 Hz, 2H), 8.30 (d, J=7.4 Hz, 2H), 7.73 (d, J=8.3 Hz, 1H), 7.01 (dd, J=11.3, 3.0 Hz, 2H), 5.05 (s, 2H). Tr(METCR0990)=0.85 min, (ES$^+$) (M+H)$^+$227.

Step 3, Method 5: 5-[(5-Methoxypyridin-2-yl)methoxy]-2-(pyridin-4-yl)-2,3-dihydro-1H-isoindol-1-one (5-Methoxypyridin-2-yl)methanol (95%, 18 mg, 0.13 mmol) was dissolved in anhydrous dichloromethane (3 mL), thionyl dichloride (61 µl, 0.84 mmol) was added and the reaction was heated to 50° C. under a nitrogen atmosphere for 2 hours. The reaction mixture was cooled to room temperature, concentrated in vacuo to give a brown oil which was used crude in the following step. 5-Hydroxy-2-(pyridin-4-yl)-2,3-dihydro-1H-isoindol-1-one (19 mg, 0.08 mmol) and 2-(chloromethyl)-5-methoxypyridine (20 mg, 0.13 mmol) were dissolved in anhydrous N,N-dimethylformamide (2 mL), sodium hydride (60%, 40.19 mg, 1 mmol) was added and the reaction was stirred overnight at room temperature under a nitrogen atmosphere. The reaction mixture was quenched with the addition of water (5 mL) and filtered, washed with water (3 mL), heptane (5 mL) and methanol (2 mL) and dried in a vacuum oven to give the title compound 7 mg (24% yield) as a brown powder.

Example 1 Method 5: 5-[(5-Methoxypyridin-2-yl)methoxy]-2-(pyridin-4-yl)-2,3-dihydro-1H-isoindol-1-one $\delta_H$ NMR (500 MHz, DMSO) 8.56-8.48 (m, 2H), 8.31 (d, J=2.9 Hz, 1H), 7.90-7.85 (m, 2H), 7.74 (d, J=8.5 Hz, 1H), 7.52 (d, J=8.6 Hz, 1H), 7.44 (dd, J=8.6, 2.9 Hz, 1H), 7.31 (d, J=1.6 Hz, 1H), 7.19 (dd, J=8.5, 2.1 Hz, 1H), 5.24 (s, 2H), 4.97 (s, 2H), 3.84 (s, 3H). Tr(MET-uHPLC-AB-101)=1.59 min, (ES$^+$) (M+H)$^+$ 348.

The following example was prepared using Method 5 described above:

TABLE 5

| Ex. | Structure | Mol. Weight | IUPAC Name | LCMS data |
|---|---|---|---|---|
| 1 | 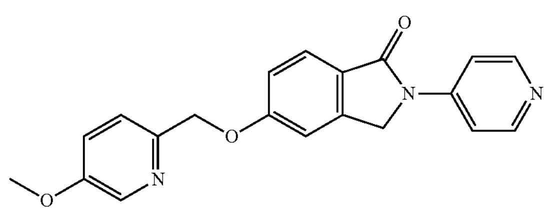 [SMILES: COc1ccc(COc2ccc3c(c2)CN(c2ccncc2)C3=O)nc1] | 347.37 | 5-[(5-Methoxypyridin-2-yl)methoxy]-2-(pyridin-4-yl)-2,3-dihydro-1H-isoindol-1-one | Tr(MET-uHPLC-AB-101) = 1.59 min, m/z (ES$^+$) (M + H)$^+$ 348 |

Biology Examples

Q46 Radioligand Binding Assay

For radioligand binding assays (RBA) GST-Q46 protein was generated based on a previous publication (Scherzinger et al. Cell, Vol. 90, 549-558, Aug. 8, 1997). For experiments 33 μM GST-Q46 was incubated with 150 μg/ml thrombin in assay buffer (150 mM NaCl, 50 mM Tris pH 8.0) and 2 mM $CaCl_2$ for 16 hr at 37° C. Aggregated Q46 was pelleted by centrifugation for 5 min at 13,000 rpm in a bench top centrifuge and re-dissolved in the same volume of assay buffer. Test compounds were prepared by titration in DMSO at 11 concentrations from 33 μM to 1 nM. For the RBA, Q46 protein aggregates and test compounds were pre-incubated in assay buffer for 20 min at room temperature, in 140 μL/well in a 96-well plate (pp, round bottom). Then, ligand was added in 10 μL/well and incubated for 60 minutes at 37° C. Final assay concentrations were 1 μM to 30 μM test compound, 5 μM Q46 protein (equivalent monomer concentration) and 10 nM ligand [$^3H_3$]MK-3328 (Harrision et al., ACS Med Chem. Lett., 2 (2011), pp 498-502). Samples were transferred onto GF/B filter plates and washed 2× with 200 μL PBS using a Filtermate Harvester. After drying filter plates for 1 hour at 37° C., the back of the plates was sealed with foil and 30 μL/well scintillation fluid (Packard MicroScint 40) was added, incubated for 15 min in the dark and counted in a TopCount reader. For analysis, replicate data from independent assay plates were normalized towards 0% and 100% inhibition using control wells of vehicle (0% inhibition) and 3 μM unlabelled MK-3328 (100% inhibition). $IC_{50}$ values were determined with a sigmoidal inhibition model with four variables (top, bottom, slope, $IC_{50}$) in a global fit using the normalized replicate data.

| Structure | IUPAC Name | Activity |
|---|---|---|
| 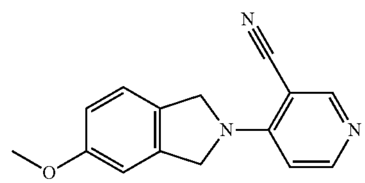 [SMILES: COc1ccc2c(c1)CN(c1ccncc1C#N)C2] | 4-(5-methoxy-2,3-dihydro-1H-isoindol-2-yl)pyridine-3-carbonitrile | +++ |
| 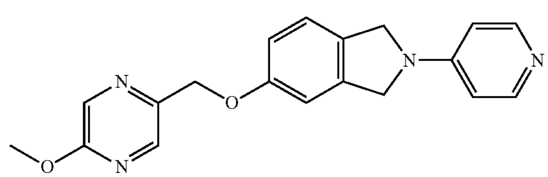 [SMILES: COc1cnc(COc2ccc3c(c2)CN(c2ccncc2)C3)cn1] | 5-[(5-methoxypyrazin-2-yl)methoxy]-2-(pyridin-4-yl)-2,3-dihydro-1H-isoindole | +++ |
| 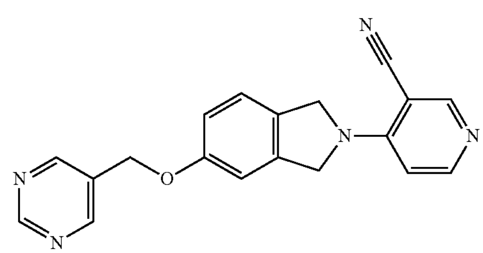 [SMILES: N#Cc1cnccc1N1Cc2ccc(OCc3cncnc3)cc2C1] | 4-[5-(pyrimidin-5-ylmethoxy)-2,3-dihydro-1H-isoindol-1-yl]pyridine-3-carbonitrile | +++ |
| 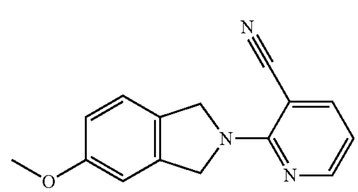 [SMILES: COc1ccc2c(c1)CN(c1ncccc1C#N)C2] | 2-(5-methoxy-2,3-dihydro-1H-isoindol-2-yl)pyridine-3-carbonitrile | +++ |
| 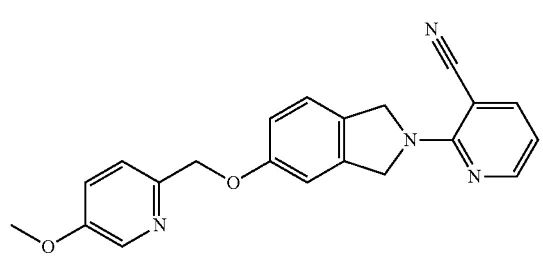 [SMILES: COc1ccc(COc2ccc3c(c2)CN(c2ncccc2C#N)C3)nc1] | 2-{5-[(5-methoxypyridin-2-yl)methoxy]-2,3-dihydro-1H-isoindol-2-yl}pyridine-3-carbonitrile | +++ |

-continued

| Structure | IUPAC Name | Activity |
|---|---|---|
| 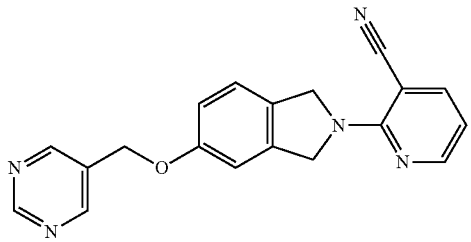 [SMILES: N#Cc1cccnc1N1Cc2ccc(OCc3cncnc3)cc2C1] | 2-[5-(pyrimidin-5-ylmethoxy)-2,3-dihydro-1H-isoindol-2-yl]pyridine-3-carbonitrile | +++ |
| 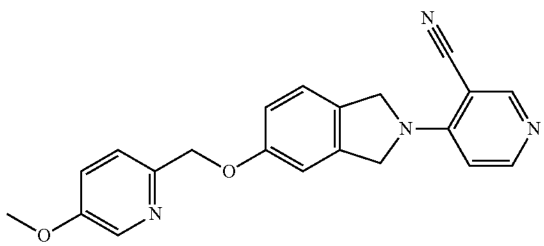 [SMILES: COc1ccc(COc2ccc3c(c2)CN(c2ccncc2C#N)C3)nc1] | 4-{5-[(5-methoxypyridin-2-yl)methoxy]-2,3-dihydro-1H-isoindol-2-yl}pyridine-3-carbonitrile | +++ |
| 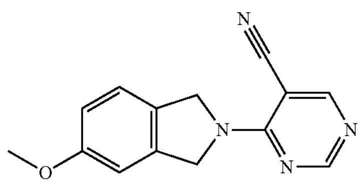 [SMILES: COc1ccc2c(c1)CN(c1ncncc1C#N)C2] | 4-(5-methoxy-2,3-dihydro-1H-isoindol-2-yl)pyrimidine-5-carbonitrile | +++ |
| 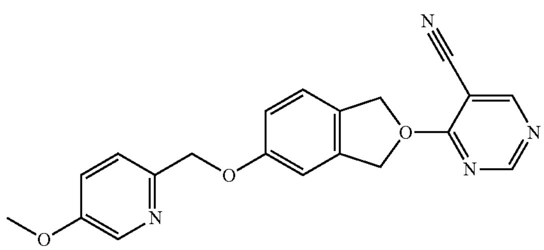 | 4-{5-[(5-methoxypyridin-2-yl)methoxy]-2,3-dihydro-1H-isoindol-2-yl}pyrimidine-5-carbonitrile | +++ |
| 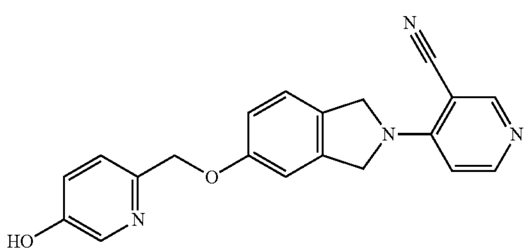 [SMILES: N#Cc1cnccc1N1Cc2ccc(OCc3ccc(O)cn3)cc2C1] | 4-{5-[(5-hydroxypyridin-2-yl)methoxy]-2,3-dihydro-1H-isoindol-2-yl}pyridine-3-carbonitrile | +++ |
| 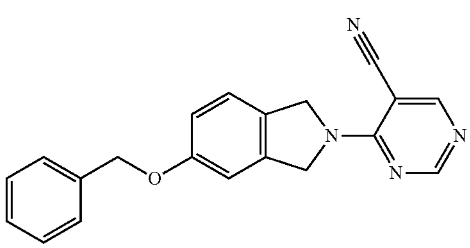 [SMILES: N#Cc1cncnc1N1Cc2ccc(OCc3ccccc3)cc2C1] | 4-[5-(benzyloxy)-2,3-dihydro-1H-isoindol-2-yl]pyrimidine-5-carbonitrile | +++ |

| Structure | IUPAC Name | Activity |
|---|---|---|
| 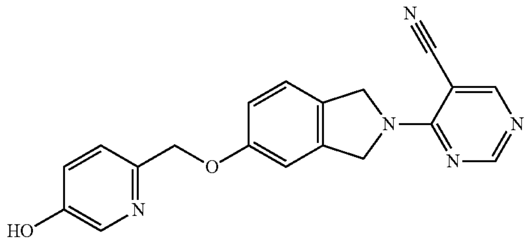 [SMILES: N#Cc1cncnc1N1Cc2ccc(OCc3ccc(O)cn3)cc2C1] | 4-{5-[(5-hydroxypyridin-2-yl)methoxy]-2,3-dihydro-1H-isoindol-2-yl}pyrimidine-5-carbonitrile | +++ |
| 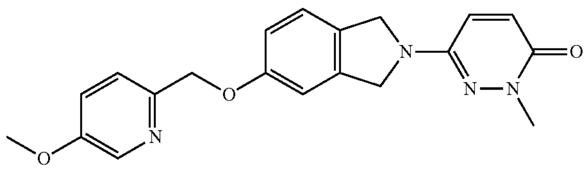 [SMILES: COc1ccc(COc2ccc3c(c2)CN(c2ccc(=O)n(C)n2)C3)nc1] | 6-{5-[(5-methoxypyridin-2-yl)methoxy]-2,3-dihydro-1H-isoindol-2-yl}-2-methyl-2,3-dihydropyridazin-3-one | +++ |
| 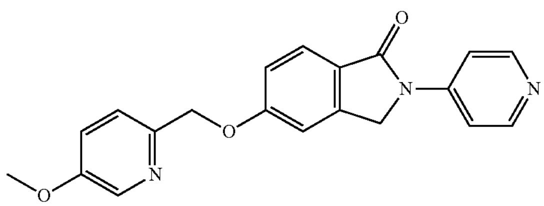 [SMILES: COc1ccc(COc2ccc3c(c2)CN(c2ccncc2)C3=O)nc1] | 5-[(5-methoxypyridin-2-yl)methoxy]-2-(pyridin-4-yl)-2,3-dihydro-1H-isoindol-1-one | +++ |

RBA IC$_{50}$ summary: <100 nM +++, 100-500 nM ++, >500 nM +

Various modifications, additions, substitutions, and variations to the illustrative examples set forth herein will be apparent to those skilled in the art from the foregoing description. Such modifications are also intended to fall within the scope of the appended claims.

What is claimed is:

1. An imaging agent comprising a compound of Formula

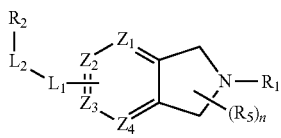

or a pharmaceutically acceptable salt thereof, wherein
$Z_1$, $Z_2$, $Z_3$, and $Z_4$ are independently chosen from C, CH, and N, provided that one of $Z_1$, $Z_2$, $Z_3$, and $Z_4$ is C and at least one of $Z_1$, $Z_2$, $Z_3$, and $Z_4$ is CH;
$R_1$ is 2,3-dihydropyridazin-3-one-6-yl optionally substituted with lower alkyl;
$L_1$ is O;
$L_2$ is $(CH_2)_m$ where m is 1 or 2;
$R_2$ is heteroaryl or heteroaryl substituted with hydroxyl or lower alkoxy;
$R_5$ is oxo; and
n is 0 or 1;
wherein the compound, or a pharmaceutically acceptable salt thereof, is labeled with one or more positron-emitting radionuclides.

2. The imaging agent of claim 1, wherein m is 1.

3. The imaging agent of claim 1, wherein $R_2$ is heteroaryl substituted with hydroxyl or lower alkoxy.

4. The imaging agent of claim 1, wherein $R_2$ is pyridin-2-yl, pyrimidin-5-yl, pyrazin-2-yl, and pyrimidin-5-yl, each of which is optionally substituted with hydroxyl or lower alkoxy.

5. The imaging agent of claim 1, wherein three of $Z_1$, $Z_2$, $Z_3$, and $Z_4$ are CH and one is C.

6. The imaging agent of claim 1, wherein $Z_1$ is N, two of $Z_2$, $Z_3$, and $Z_4$ are CH and one is C.

7. The imaging agent of claim 1, wherein $Z_2$ is N and $Z_1$, $Z_3$, and $Z_4$ are CH or C.

8. The imaging agent of claim 1, wherein $Z_2$ and $Z_4$ are one of $Z_1$ and $Z_3$ is CH and the other is C.

9. An imaging agent comprising a compound chosen from:
2-(5-methoxy-2,3-dihydro-1H-isoindol-2-yl)pyridine-3-carbonitrile;
2-{5-[(5-methoxypyridin-2-yl)methoxy]-2,3-dihydro-1H-isoindol-2-yl}pyridine-3-carbonitrile;
2-[5-(pyrimidin-5-ylmethoxy)-2,3-dihydro-1H-isoindol-2-yl]pyridine-3-carbonitrile;
4-{5-[(5-methoxypyridin-2-yl)methoxy]-2,3-dihydro-1H-isoindol-2-yl}pyridine-3-carbonitrile;
4-(5-methoxy-2,3-dihydro-1H-isoindol-2-yl)pyrimidine-5-carbonitrile;
4-{5-[(5-methoxypyridin-2-yl)methoxy]-2,3-dihydro-1H-isoindol-2-yl}pyrimidine-5-carbonitrile;
4-{5-[(5-hydroxypyridin-2-yl)methoxy]-2,3-dihydro-1H-isoindol-2-yl}pyridine-3-carbonitrile;
4-(5-methoxy-2,3-dihydro-1H-isoindol-2-yl)pyridine-3-carbonitrile;
4-[5-(pyrimidin-5-ylmethoxy)-2,3-dihydro-1H-isoindol-2-yl]pyridine-3-carbonitrile;
5-[(5-methoxypyrazin-2-yl)methoxy]-2-(pyridin-4-yl)-2,3-dihydro-1H-isoindole;
4-[5-(benzyloxy)-2,3-dihydro-1H-isoindol-2-yl]pyrimidine-5-carbonitrile;
4-{5-[(5-hydroxypyridin-2-yl)methoxy]-2,3-dihydro-1H-isoindol-2-yl}pyrimidine-5-carbonitrile;
6-{5-[(5-methoxypyridin-2-yl)methoxy]-2,3-dihydro-1H-isoindol-2-yl}-2-methyl-2,3-dihydropyridazin-3-one; and 5-[(5-methoxypyridin-2-yl)methoxy]-2-(pyridin-4-yl)-2,3-dihydro-1H-isoindol-1-one;

or a pharmaceutically acceptable salt thereof, and wherein the compound is labeled with one or more positron-emitting radionuclides.

10. The imaging agent of claim 1, wherein said compound contains one or more positron-emitting radionuclides selected from: $^{11}$C, $^{13}$N, $^{15}$O, and $^{18}$F.

11. A method of generating diagnostic images in an individual comprising administering an effective amount of an imaging agent of claim 1 to an individual, and generating an image of at least a part of said individual.

12. The method of claim 11, wherein generating an image of at least a part of said individual comprises generating an image to detect the presence or absence of huntingtin protein (HTT protein) aggregates in the brain of said individual; and detecting the presence or absence of a pathologic process.

13. The method of claim 12, wherein said HTT protein aggregates are present in the basal ganglia of said brain of said individual.

14. The method of claim 12, wherein the pathologic process is a neurodegenerative disease.

15. The method of claim 14, wherein the neurodegenerative disease is chosen from Alzheimer's disease, amyotrophic lateral sclerosis, Huntington's disease, Parkinson's disease, Prion disease and spinocerebellar ataxias.

16. The method of claim 15, wherein the neurodegenerative disease is Huntington's disease (HD).

17. The method of claim 11, wherein said effective amount of said imaging agent comprises from about 0.1 to about 20 mCi.

18. The method of claim 17, wherein said effective amount of said imaging agent comprises about 10 mCi.

19. The method of claim 11, wherein said generating an image comprises positron emission tomography (PET) imaging, PET with concurrent computed tomography imaging (PET/CT), PET with concurrent magnetic resonance imaging (PET/MRI), or a combination thereof.

20. The method of claim 19, wherein said generating an image comprises PET imaging.

* * * * *

UNITED STATES PATENT AND TRADEMARK OFFICE
CERTIFICATE OF CORRECTION

| | |
|---|---|
| PATENT NO. | : 11,071,793 B2 |
| APPLICATION NO. | : 15/507214 |
| DATED | : July 27, 2021 |
| INVENTOR(S) | : Dominguez et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 64 days.

Signed and Sealed this
Twenty-fourth Day of January, 2023

Katherine Kelly Vidal
*Director of the United States Patent and Trademark Office*